United States Patent [19]

Jamas et al.

[11] Patent Number: 5,783,569
[45] Date of Patent: Jul. 21, 1998

[54] USES FOR UNDERIVATIZED, AQUEOUS SOLUBLE β(1-3) GLUCAN AND COMPOSITIONS COMPRISING SAME

[75] Inventors: Spiros Jamas, Boston; D. Davidson Easson, Jr., Shrewsbury; Gary R. Ostroff, Worcester, all of Mass.

[73] Assignee: Alpha-Beta Technology, Inc., Worcester, Mass.

[21] Appl. No.: 373,251

[22] PCT Filed: Aug. 20, 1993

[86] PCT No.: PCT/US93/07904

§ 371 Date: Jan. 26, 1995

§ 102(e) Date: Jan. 26, 1995

[87] PCT Pub. No.: WO94/04163

PCT Pub. Date: Mar. 3, 1994

Related U.S. Application Data

[63] Continuation-in-part of Ser. No. 934,015, Aug. 21, 1992, Pat. No. 5,622,939.

[51] Int. Cl.⁶ .............. C07H 1/00; C08B 37/00; A61K 31/715
[52] U.S. Cl. .............. 514/54; 536/123.12; 536/123.1; 536/124
[58] Field of Search .............. 514/54; 536/123.12, 536/123.1, 124

[56] References Cited

U.S. PATENT DOCUMENTS

| | | | |
|---|---|---|---|
| 4,138,479 | 2/1979 | Truscheit et al. | 424/88 |
| 4,237,266 | 12/1980 | Sugiura et al. | 536/1 |
| 4,707,471 | 11/1987 | Larm et al. | 514/54 |

(List continued on next page.)

FOREIGN PATENT DOCUMENTS

| | | |
|---|---|---|
| 0463540 | 1/1992 | European Pat. Off. |
| 55-071701 | 8/1980 | Japan . |
| 56-076401 | 9/1981 | Japan . |
| 59-045301 | 6/1984 | Japan . |
| 59210901 | 4/1995 | Japan . |
| 2076418 | 12/1981 | United Kingdom . |
| 91/03248 | 3/1991 | WIPO . |
| 91/03495 | 3/1991 | WIPO . |
| 92/13896 | 8/1992 | WIPO . |
| 94/03498 | 2/1994 | WIPO . |
| 94/03500 | 2/1994 | WIPO . |

OTHER PUBLICATIONS

Jamas et al., "PGG–A Novel Class of Macrophage Activating Immunomodulators", *Polymer Preprints* 31:194–195, Aug. 8, 1990.

(List continued on next page.)

*Primary Examiner*—John Kight
*Assistant Examiner*—Everett White
*Attorney, Agent, or Firm*—Hamilton, Brook, Smith & Reynolds, P.C.

[57] ABSTRACT

The present invention relates to neutral, aqueous soluble β-glucans which exert potent and specific immunological effects without stimulating the production of certain cytokines, to preparations containing the novel β-glucans, and to a novel manufacturing process therefor. The neutral, aqueous soluble β-glucan preparation has a high affinity for the β-glucans receptor of human monocytes and retains two primary biological (or immunological) activities, (1) the enhancement of microbicidal activity of phagocytic cells, and (2) monocyte, neutrophil and platelet hemopoietic activity. Unlike soluble glucans described in the prior art, the neutral, aqueous soluble β-glucans of this invention neither induces nor primes IL-1β and TNFα production in vitro and in vivo. Safe and efficacious preparations of neutral, aqueous soluble β-glucan of the present invention can be used in therapeutic and/or prophylactic treatment regimens of humans and animals to enhance their immune response, without stimulating the production of certain biochemical mediators (e.g., IL-1β, TNFα) that can cause detrimental side effects, such as fever and inflammation.

87 Claims, 7 Drawing Sheets

U.S. PATENT DOCUMENTS

| | | | |
|---|---|---|---|
| 4,739,046 | 4/1988 | DiLuzio et al. | 536/117 |
| 4,761,402 | 8/1988 | Williams et al. | 514/54 |
| 4,810,646 | 3/1989 | Jamas et al. | 435/101 |
| 5,032,401 | 7/1991 | Jamas et al. | 424/426 |
| 5,057,503 | 10/1991 | Czop et al. | 514/54 |
| 5,320,849 | 6/1994 | Hagiwara et al. | 424/442 |
| 5,322,841 | 6/1994 | Jamas et al. | 514/54 |
| 5,622,939 | 4/1997 | Jamas et al. | 514/54 |

OTHER PUBLICATIONS

Janusz, M.J. et al., "Isolation of Soluble Yeast ⊕–Glucans That Inhhibit Human Monocyte Phagocytosis Mediated by β–Glucan Receptors," *J. Immunol. 137:* 3270–3276 (Nov. 15, 1986).

Manners, D.J. et al., "The Structure of a β–(1→3)–D–Glucan from Yeast Cell Walls," *Biochem. J. 135:* 19–30 (1973).

Fleet, G.H., et al., "Isolation and Composition of an Alkali–Soluble Glucan from the Cell Walls of *Saccharomyces cerevisiae*," *Journal of General Microbiology, 94:* 180–192 (1976).

Miyazaki, T., et al., "Structural Examination of Antitumour, Water–Soluble Glucans from *Grifora umbellata* by Use of Four Types of Glucanase," *Carbohydrate Research, 65:* 234–243 (1978).

Reiskind, J.B. and Mullins, J.T., "Molecular Architecture of the Hyphal Wall of *Achlya ambisexualis* Raper. II. Ultrastructural Analyses and a Proposed Model," *Can. J. Microbiol., 27:* 1100–1105 (1981).

Latgé, J.P. et al., "Composition Chimique et Ultrastructure des Parois des Corps Hyphaux et des Azygospores de *Conidiobolus obscurus,*" *Can. J. Microbiol., 30:* 1507–1521 (1984).

Sherwood, E.R. et al., "Soluble Glucan and Lymphokine–Activated Killer (LAK) Cells in The Therapy of Experimental Hepatic Metastases," *Chemical Abstracts 108:* 179752v (1988).

Hara, C. et al., "A Branched (1→3)–β–D–Glucan from a Water Extract of *Dictyophora indusiata* FISCH," *Carb. Res. 145:* 237–246 (1986).

Goldman, R., "Induction of a β–1,3–D–Glucan Receptor in P388D1 Cells Treated with Retinoic Acid of 1,25–dihydroxyvitamin $D_3$," *Immunology 63:* 319–324 (1988).

Konopski, A. et al., "Phagocytosis of β–1,3–D–Glucan–Derivatized Microbeads by Mouse Peritoneal Macrophages Involves Three Different Receptors," *Scand. J. Immunol. 33:* 297–306 (1991).

Williams, D.L. et al., "Development of a Water–Soluble, Sulfated (1→3)–β–D–Glucan Biological Response Modifier Derived from *Saccharomyces cerevisiae,*" *Carbohydrate Research 235:* 247–257 (1992).

Williams, D.L. et al., "A Sequential Multi-Assay Protocol for the Preclinical Assessment of Natural Product Complex Carbohydrate Immunomodulators," *Develop. Biol. Standard, 77:* 129–136 (1992).

Williams, D.L. et al., "Development, Physicochemical Characterization and Preclinical Efficacy Evaluation of a Water Soluble Glucan Sulfate Derived from *Saccharomyces cerevisiae,*" *Immunopharmacology 22:* 139–156 (1991).

Pretus, H.A. et al., "Isolation, Physiochemical Characterization and Preclinical Efficacy Evaluation of Soluble Scleroglucan," *The J. of Pharmacol. and Exp. Therap.* 257:500–510 (1991).

Bacon, J. et al., "The Glucan Components of the Cell Wall of Baker's Yeast *(Saccharomyces cerevisiae)* Considered in Relation to its Ultrastructure," *Biochem. J. 114:* 557–567 (1969).

*Vestnik Federalniho Uradu Pro Vynalezy* 10: 111 (1989).

*Vestnik Federalniho Uradu Pro Vynalezy* 11: 122–123 (1989).

Onderdonk, A.B. et al., "Anti–Infective Effect of Poly–β1–6–Glucotrisyl–β1–3–Glucopyranose Glucan In Vivo," *Infect. Immun. 60:* 1642–1647 (1992).

Abel, G. and J.K. Czop, "Activaiton of Human Monocyte GM–CSF and TNF–Aα Production by Particulate Yeast Glucan," International Congress for Infectious Diseases, Montreal Canada (Abstract), Jul. 15–19, 1990.

Chihara, G. et al., "Lentinan as a Host Defense Potentiator (HPD)," *Int. J. Immunotherapy V(4):* 145–154 (1989).

Sherwood, E.R. et al., "Enhancement of Interleukin–1 and Interleukin–2 Production by Soluble Glucan," *Int. J. Immunopharm. 9(3):* 261–267 (1987).

Williams, D.L. et al., "Pre–Clinical Safety Evaluation of Soluble Glucan," *Int. J. Immunopharmac. 10(4):* 405–414 (1988).

Browder, W. et al., "Beneficial Effect of Enhanced Macrophage Function in the Trauma Patient," *Ann. Surg.* pp. 605–613 (1990).

Jamas et al, "A Novel Class of Macrophage–Activating Immunomodulators" ACS Symposium Series, *Polymeric Drugs and Delivery Systems,* Chapter 5 pp. 44–45 (1991).

Shiota, M. et al., "Comparison of β–Glucan Structures in a Cell Wall Mutant of *Saccharomyces cerevisiae* and the Wild Type", *J. Biochem.* 98:1301–1307 (1985).

Jamas et al., "PGG–A Novel Class of Macrophage Activating Immunomodulators", International Congress for Infectious Diseases, Montreal Canada (Abstract), Jul. 15–19, 1990.

Katzen et al., "PGG, A Glucose Polymer, Primes Interleukin–1 and Tumor Necrosis Factor Production . . . ", International Congress for Infectious Diseases, Montreal Canada (Abstract), Jul. 15–19, 1990.

Shah et al., "Influence of PGG on the Phagocytosis of *Staphylococcus aureus* or *Escherichia coli...*" International Congress for Infectious Diseases, Montreal Canada (Abstract), Jul. 15–19, 1990.

Onderdonk, A.B., "Effect of a New Carbohydrate Polymer on Servival in a Mouse Model for Experimental *E. coli* sepsis", International Congress for Infectious Diseases, Montreal Canada (Abstract), Jul. 15–19, 1990.

A. Arbo and J.L. Santos, "Effect of PGG on Neutrophil (PMN) Function in Experimental Malnutrition", International Congress for Infectious Diseases, Montreal Canada (Abstract), Jul. 15–19, 1990.

Onderdonk et al., "Protective Effect of a New Carbohydrate Polymer in a Rat Model for Experimental Intraabdominal Sepsis", First International Congress on Biological Responses Modifies, (Abstract) Quebec Canada, Mar. 22–14, 1991.

Sakurai et al., "Intravenously Administered (1→3)–β–D–Glucan, SSG, Obtained from *Sclerotinia sclerotiorum* IFO 9395 . . . ", *Chem. Pharm. Bull.* 40(8):2120–2124 (1992).

P.H. Lagrange and M. Fourgeaud, "Enhanced Natural Resistance Against Severe Disseminated *Candida albicans*. . . ", *Int'l. J. of Experimental and Clin. Chemotherapy* 4(1):48–55(1991).

USES FOR UNDERIVATIZED, AQUEOUS SOLUBLE β(1-3) GLUCAN AND COMPOSITIONS COMPRISING SAME

RELATED APPLICATIONS

This is a U.S. National Phase of PCT/US93/07904 filed Aug. 20, 1993, which is a continuation-in-part of application U.S. Ser. No. 07/934,015 filed on Aug. 21, 1992, now U.S. Pat. No. 5,622,939.

BACKGROUND OF THE INVENTION

In the early 1960's, zymosan, a crude insoluble yeast extract prepared by boiling yeast before and after trypsin treatment, was noted to produce marked hyperplasia and functional stimulation of the reticuloendothelial system in rodents. In animal studies, zymosan preparations were shown to inactivate complement component C3, to enhance antibody formation, to promote survival following irradiation, to increase resistance to bacterial infections, to inhibit tumor development, to promote graft rejection, and to inhibit dietary-induced hypercholesterolemia and cholesterosis. Zymosan was shown to consist of polysaccharides, proteins, fats, and inorganic elements; however, subsequent studies identified the active components of the yeast cell wall as a pure polysaccharide, specifically β-glucan. In conventional nomenclature, the polysaccharide β-glucan is known as poly-(1-6)-β-D-glucopyranosyl-(1-3)-β-D-glucopyranose (PGG). Repetition of biological assays with β-glucan indicated that most of the above functional activities identified with zymosan were retained by the purified β-glucan preparation.

The properties of β-glucan are quite similar to those of endotoxin in increasing nonspecific immunity and resistance to infection. The activities of β-glucan as an immune adjuvant and hemopoietic stimulator compare to those of more complex biological response modifiers (BRMs), such as bacillus Calmette-Guerin (BCG) and *Corynebacterium parvum*. The functional activities of yeast β-glucan are also comparable to those structurally similar carbohydrate polymers isolated from fungi and plants. These higher molecular weight (1-3)-β-D-glucans such as schizophyllan, lentinan, krestin, grifolan, and pachyman exhibit similar immunomodulatory activities. A common mechanism shared by all these β-glucan preparations is their stimulation of cytokines such as interleukin-1 (IL-1) and tumor necrosis factor (TNF). Lentinan has been extensively investigated for its antitumor properties, both in animal models at 1 mg/kg for 10 days and in clinical trials since the late 1970s in Japan for advanced or recurrent malignant lymphoma and colorectal, mammary, lung and gastric cancers. In cancer chemotherapy, lentinan has been administered at 0.5–5 mg/day, intramuscularly (I.M.) or intravenously (I.V.), two or three times per week alone, or in combination with antineoplastic drugs. In addition to the activities ascribed to yeast glucans, studies suggest lentinan acts as a T-cell immunopotentiator, inducing cytotoxic activities, including production of interleukins 1 and 3 and colony-stimulating factors (CSF). (Chihara et al., 1989, *Int. J. Immunotherapy*, 4:145–154; Hamuro and Chihara, In *Lentinan. An Immunopotentiator*)

Various preparations of both particulate and soluble β-glucans have been tested in animal models to evaluate biological activities. The use of soluble and insoluble β-glucans alone or as vaccine adjuvants for viral and bacterial antigens has been shown in animal models to markedly increase resistance to a variety of bacterial, fungal, protozoan and viral infections. The hemopoietic effects of β-glucan have been correlated with increased peripheral blood leukocyte counts and bone marrow and splenic cellularity, reflecting increased numbers of granulocyte-macrophage progenitor cells, splenic pluripotent stem cells, and erythroid progenitor cells, as well as, increased serum levels of granulocyte-monocyte colony-stimulating factor (GM-CSF). Furthermore, the hemopoietic and anti-infective effects of β-glucan were active in cyclophosphamide-treated immunosuppressed animals. β-glucan was shown to be beneficial in animal models of trauma, wound healing and tumorigenesis. However, various insoluble and soluble preparations of β-glucan differed significantly in biological specificity and potency, with effective dosages varying from 25 to 500 mg/kg intravenously or intraperitoneally (I.P.) in models for protection against infection and for hemopoiesis. Insoluble preparations demonstrated undesirable toxicological properties manifested by hepatosplenomegaly and granuloma formation. Clinical interest was focused on a soluble glucan preparation which would retain biological activity yet yield negligible toxicity when administered systemically. Chronic systemic administration of a soluble phosphorylated glucan over a wide range of doses (40–1000 mg/kg) yielded negligible toxicity in animals (DiLuzio et al., 1979, *Int. J. of Cancer*, 24:773–779; DiLuzio, U.S. Pat. No. 4,739,046).

The molecular mechanism of action of β-glucan has been elucidated by the demonstration of specific β-glucan receptor binding sites on the cell membranes of human neutrophils and macrophages. Mannans, galactans, α(1-4)-linked glucose polymers and β(1-4)-linked glucose polymers have no avidity for this receptor. These β-glucan binding sites are opsonin-independent phagocytic receptors for particulate activators of the alternate complement pathway, similar to *Escherichia coli* lipopolysaccharide (LPS) and some animal red blood cells. Ligand binding to the β-glucan receptor, in the absence of antibody, results in complement activation, phagocytosis, lysosomal enzyme release, and prostaglandin, thromboxane and leukotriene generation; thereby increasing nonspecific resistance to infection. However, soluble β-glucan preparations described in the prior art demonstrated stimulation of cytokines. Increases in plasma and splenic levels of interleukins 1 and 2 (IL-1, IL-2) in addition to TNF were observed in vivo and corresponded to induction of the synthesis of these cytokines iL vitro. (See Sherwood et al., 1987, *Int. J. Immunopharmac.*, 9:261–267 (enhancement of IL-1 and IL-2 levels in rats injected with soluble glucan); Williams et al., 1988, *Int. J. Immunopharmac.*, 10:405–414 (systemic administration of soluble glucan to AIDS patients increased IL-1 and IL-2 levels which were accompanied by chills and fever); Browder et al., 1990, *Ann. Surg.*, 211:605–613 (glucan administration to trauma patients increased serum IL-1 levels, but not TNF levels); Adachi et al., 1990, *Chem. Pharm. Bull.*, 38:988–992 (chemically cross-linked β(1-3) glucans induced IL-1 production in mice).)

Interleukin-1 is a primary immunologic mediator involved in cellular defense mechanisms. Numerous studies have been carried out on the application of IL-1 to enhance non-specific resistance to infection in a variety of clinical states. Pomposelli et al., *J. Parent. Ent. Nutr.* 12(2):212–218, (1988). The major problem associated with the excessive stimulation or exogenous administration of IL-1 and other cellular mediators in humans is toxicity and side effects resulting from the disruption of the gentle balance of the immunoregulatory network. Fauci et al., *Ann. Int. Med.*, 106:421–433 (1987). IL-1 is an inflammatory cytokine that has been shown to adversely affect a variety of tissues and organs. For instance, recombinant IL-1 has been shown to cause death, hypotensive shock, leukopenia, thrombocytopenia, anemia and lactic acidosis. In addition, IL-1 induces sodium excretion, anorexia, slow wave sleep, bone resorption, decreased pain threshold and expression of many inflammatory-associated cytokines. It is also toxic to the insulin secreting beta cells of the pancreas. Patients suffering from a number of inflammatory diseases have elevated levels of IL-1 in their systems. Administration of agents that enhance further IL-1 production only exacerbate these inflammatory conditions.

Tumor necrosis factor is also involved in infection, inflammation and cancer. Small amounts of TNF release growth factors while in larger amounts, TNF can cause septic shock, aches, pains, fever, clotting of blood, degradation of bone and stimulation of white blood cells and other immune defenses.

SUMMARY OF THE INVENTION

The present invention relates to neutral soluble β-glucans which enhance a host's immune defense mechanisms to infection but do not induce an inflammatory response, to preparations containing the neutral soluble β-glucans, and to a novel manufacturing process therefor. In the present method, soluble glucan which induces cytokine production is processed through a unique series of acid, alkaline and neutral treatment steps to yield a conformationally pure neutral soluble glucan preparation with unique biological properties. The neutral soluble glucan preparation retains a specific subset of immunological properties common to β-glucans but uniquely does not induce the production of IL-1 and TNF in vitro or in vivo. Throughout this specification, unless otherwise indicated, the expressions "neutral soluble glucan" and "neutral soluble β-glucan" refer to the composition prepared as described in Example 1.

The neutral soluble glucan preparation is produced by treating insoluble glucan with acid to produce a water soluble glucan, dissociating the native conformations of the soluble glucan at alkaline pH, purifying the desired molecular weight fraction at alkaline pH, re-annealing the dissociated glucan fraction under controlled conditions of time, temperature and pH to form a unique triple helical conformation, and further purifying under neutral pH to remove single helix and aggregated materials to yield a conformationally pure, neutral, water soluble, underivatized glucan which has a unique biological profile.

The neutral soluble glucan preparation has a high affinity for the β-glucan receptor of human monocytes and retains two primary biological activities, (1) the enhancement of microbicidal activity of phagocytic cells, and (2) monocyte, neutrophil and platelet hemopoietic activity. Unlike soluble glucans described in the prior art, the neutral soluble glucan of this invention neither induces nor primes mononuclear cells to increase IL-1 and TNF production in vitro and in vivo.

The neutral soluble glucan preparation is appropriate for parenteral (e.g., intravenous, intraperitoneal, subcutaneous, intramuscular), topical, oral or intranasal administration to humans and animals as an anti-infective to combat infection associated with burns, surgery, chemotherapy, bone marrow disorders and other conditions in which the immune system may be compromised. Neutral soluble glucan produced by the present method can be maintained in a clear solution and equilibrated in a pharmaceutically acceptable carrier. Safe and efficacious preparations of the neutral soluble glucan of the present invention can be used in therapeutic and/or prophylactic treatment regimens of humans and animals to enhance their immune response, without stimulating the production of certain biochemical mediators (e.g., IL-1 and TNF) that can cause detrimental side effects, such as fever and inflammation.

DETAILED DESCRIPTION OF INVENTION

The invention relates to a neutral soluble β-glucan polymer that can bind to the β-glucan receptor and activate only a desired subset of immune responses. The terms "neutral soluble β-glucan" and "neutral soluble glucan", unless otherwise specified, refer to the composition prepared as described in Example 1.

This neutral soluble β-glucan has been shown to increase the number of neutrophils and monocytes as well as their direct infection fighting activity (phagocytosis and microbial killing). However, the neutral soluble β-glucan does not stimulate the production of biochemical mediators, such as IL-1 and TNF, that can cause detrimental side effects such as high fever, inflammation, wasting disease and organ failure. These advantageous properties make neutral soluble glucan preparations of this invention useful in the prevention and treatment of infection because they selectively activate only those components of the immune system responsible for the initial response to infection, without stimulating the release of certain biochemical mediators that can cause adverse side effects. The solution containing the neutral soluble β-glucan also lacks the toxicity common to many immunomodulators.

Figure 1:
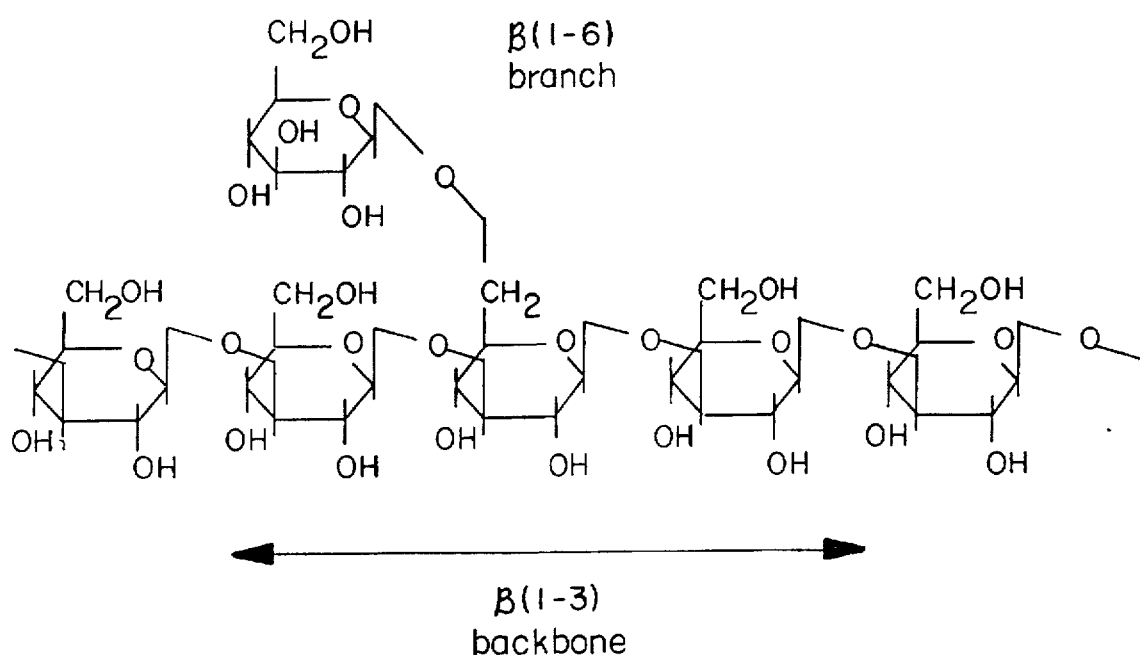
FIG. 1 shows the general structure of neutral soluble glucan as being a linear β(1-3)-linked glucose polymer having periodic branching via a single β(1-6)-linked glucose moiety.

The neutral soluble β-glucans of this invention are composed of glucose monomers organized as a β(1-3) linked glucopyranose backbone with periodic branching via β(1-6) glycosidic linkages. The neutral soluble glucan preparations contain glucans, which have not been substantially modified by substitution with functional (e.g., charged) groups or other covalent attachments. The general structure of the neutral soluble glucan is shown in FIG. 1. The biologically active preparation of this invention is a conformationally purified form of β-glucan produced by dissociating the native glucan conformations and reannealing and purifying the resulting unique triple helical conformation. The unique conformation of the neutral soluble glucan contributes to the glucan's ability to selectively activate the immune system without stimulating the production of detrimental biochemical mediators.

The neutral soluble glucan preparations of this invention are prepared from insoluble glucan particles, preferably derived from yeast organisms. See Manners et al., *Biochem. J.*, 135:19–30, (1973) for a general procedure to make insoluble yeast glucans. Glucan particles which are particularly useful as starting materials in the present invention are whole glucan particles (WGP) described by Jamas et al., in U.S. Pat. Nos. 4,810,646, 4,992,540, 5,082,936 and 5,028,703, the teachings of all of which are hereby incorporated herein by reference. The source of the whole glucan particles can be the broad spectrum of glucan-containing yeast organisms which contain β-glucans in their cell walls. Whole glucan particles obtained from the strains *Saccharomyces cerevisiae* R4 (NRRL Y-15903; deposit made in connection with U.S. Pat. No. 4,810,646) and R4 Ad (ATCC No. 74181) are particularly useful. Other strains of yeast that can be used include *Saccharomyces delbrueckii, Saccharomyces rosei, Saccharomyces microellinsodes, Saccharomyces carlsbergensis, Schizosaccharomyces pombe, Kluyveromyces lactis, Kluyveromyces fragilis, Kluyveromyces polysporus, Candida albicans, Candida cloacae, Candida tropicalis, Candida utilis, Hansenula wingei, Hansenula arni, Hansenula henricii, Hansenula americana*.

A procedure for extraction of whole glucan particles is described by Jamas et al., in U.S. Pat. Nos. 4,810,646, 4,992,540, 5,082,936 and 5,028,703. For the purpose of this present invention, it is not necessary to conduct the final organic extraction and wash steps described by Jamas et al.

In the present process, whole glucan particles are suspended in an acid solution under conditions sufficient to dissolve the acid-soluble glucan portion. For most glucans, an acid solution having a pH of from about 1 to about 5 and at a temperature of from about 20 to about 100° C. is sufficient. Preferably, the acid used is an organic acid capable of dissolving the acid-soluble glucan portion. Acetic acid, at concentrations of from about 0.1 to about 5M or formic acid at concentrations of from about 50% to 98% (w/v) are useful for this purpose. The treatment time may vary from about 10 minutes to about 20 hours depending on the acid concentration, temperature and source of whole glucan particles. For example, modified glucans having more β(1-6) branching than naturally-occurring, or wild-type glucans, require more stringent conditions, i.e., longer exposure times and higher temperatures. This acid-treatment step can be repeated under similar or variable conditions. One preferred processing method is described in the exemplification using glucan derived from *S. cerevisiae* strain R4 Ad. In another embodiment of the present method, whole glucan particles from the strain, *S. cerevisiae* R4, which have a higher level of β(1-6) branching than naturally-occurring glucans, are used, and treatment is carried out with 90% (w/v) formic acid at 20° C. for about 20 minutes and then at 85° C. for about 30 minutes.

The insoluble glucan particles are then separated from the solution by an appropriate separation technique, for example, by centrifugation or filtration. The pH of the resulting slurry is adjusted with an alkaline compound such as sodium hydroxide, to a pH of about 7 to about 14. The precipitate is collected by centrifugation and is boiled in purified water (e.g., USP) for three hours. The slurry is then resuspended in hot alkali having a concentration sufficient to solubilize the glucan polymers. Alkaline compounds which can be used in this step include alkali-metal or alkali-earth metal hydroxides, such as sodium hydroxide or potassium hydroxide, having a concentration of from about 0.01 to about 10N. This step can be conducted at a temperature of from about 4° C. to about 121° C., preferably from about 20° C. to about 100° C. In one embodiment of the process, the conditions utilized are a 1M solution of sodium hydroxide at a temperature of about 80°–100° C. and a contact time of approximately 1–2 hours. The resulting mixture contains solubilized glucan molecules and particulate glucan residue and generally has a dark brown color due to oxidation of contaminating proteins and sugars. The particulate residue is removed from the mixture by an appropriate separation technique, e.g., centrifugation and/or filtration. In another embodiment of the process the acid-soluble glucans are precipitated after the preceding acid hydrolysis reaction by the addition of about 1.5 volumes of ethanol. The mixture is chilled to about 4° C. for two (2) hours and the resulting precipitate is collected by centrifugation or filtration and washed with water. The pellet is then resuspended in water, and stirred for three (3) to twelve (12) hours at a temperature between about 20° C. and 100° C. At this point the pH is adjusted to approximately 10 to 13 with a base such as sodium hydroxide.

The resulting solution contains dissociated soluble glucan molecules. This solution is now purified to remove traces of insoluble glucan and high molecular weight soluble glucans which can cause aggregation. This step can be carried out by an appropriate purification technique, for example, by ultrafiltration, utilizing membranes with nominal molecular weight (NMW) levels or cut-offs in the range of about 1,000 to 100,000 daltons. It was discovered that in order to prevent gradual aggregation or precipitation of the glucan polymers the preferred membrane for this step has a nominal molecular weight cut-off of about 100,000 daltons. The soluble glucan is then further purified at alkaline pH to remove low molecular weight materials. This step can be carried out by an appropriate purification technique, for example, by ultrafiltration, utilizing membranes with nominal molecular weight levels or cut-offs in the range of 1,000 to 30,000 daltons.

The resulting dissociated soluble glucan is re-annealed under controlled conditions of time (e.g., from about 10 to about 120 minutes), temperature (e.g., from about 50° to about 70° C.) and pH. The pH of the solution is adjusted to the range of about 3.5–11 (preferably 6–8) with an acid, such as hydrochloric acid. The purpose of this re-annealing step is to cause the soluble glucan to rearrange from a single helix conformation to a new ordered triple helical conformation. The re-annealed glucan solution is then size fractionated, for example by using 30,000–70,000 NMW and 100,000–500,000 NMW cut-off membrane ultrafilters to selectively remove high and low molecular weight soluble glucans. Prior to sizing, the soluble glucans exist as a mixture of conformations including random coils, gel matrices or aggregates, triple helices and single helices. The objective of the sizing step is to obtain an enriched fraction for the re-annealed conformation of specific molecular weight. The order in which the ultrafilters are used is a matter of preference.

The concentrated fraction obtained is enriched in the soluble, biologically active neutral soluble glucan. The glucan concentrate is further purified, for example, by diafiltration using a 10,000 dalton membrane. The preferred concentration of the soluble glucan after this step is from about 2 to about 10 mg/ml.

The neutralized solution can then be further purified, for example, by diafiltration, using a pharmaceutically acceptable medium (e.g., sterile water for injection, phosphate-buffered saline (PBS), isotonic saline, dextrose) suitable for parenteral administration. The preferred membrane for this diafiltration step has a nominal molecular weight cut-off of about 10,000 daltons. The final concentration of the glucan solution is adjusted in the range of about 0.5 to 10 mg/ml. In accordance with pharmaceutical manufacturing standards for parenteral products, the solution can be terminally sterilized by filtration through a 0.22 μm filter. The neutral soluble glucan preparation obtained by this process is sterile, non-antigenic, essentially pyrogen-free, and can be stored at room temperature (e.g., 15°–30° C.) for extended periods of time without degradation. This process is unique in that it results in a neutral aqueous solution of (pH 4.5 to 7.0) immunologically active glucans which is suitable for parenteral administration.

For purposes of the present invention, the term "soluble" as used herein to describe glucans obtained by the present process, means a visually clear solution can be formed in an aqueous medium such as water, PBS, isotonic saline, or a dextrose solution having a neutral pH (e.g., from about pH 5 to about 7.5), at room temperature (about 20°–25° C.) and at a concentration of up to about 10 mg/ml. The term "aqueous medium" refers to water and water-rich phases, particularly to pharmaceutically acceptable aqueous liquids, including PBS, saline and dextrose solutions. The expression "visually clear" means that at a concentration of 1 mg/ml, the absorption of the solution at 530 nm is less than OD 0.01 greater than the OD of an otherwise identical solution lacking the β-glucan component.

The resulting solution is substantially free of protein contamination, is non-antigenic, non-pyrogenic and is pharmaceutically acceptable for parenteral administration to animals and humans. However, if desired, the soluble glucan can be dried by an appropriate drying method, such as lyophilization, and stored in dry form.

The neutral soluble glucans of this invention can be used as safe, effective, therapeutic and/or prophylactic agents, either alone or as adjuvants, to enhance the immune response in humans and animals. Soluble glucans produced by the present method selectively activate only those components that are responsible for the initial response to infection, without stimulating or priming the immune system to release certain biochemical mediators (e.g., IL-1, TNF, IL-6, IL-8 and GM-CSF) that can cause adverse side effects. As such, the present soluble glucan composition can be used to prevent or treat infectious diseases in malnourished patients, patients undergoing surgery and bone marrow transplants, patients undergoing chemotherapy or radiotherapy, neutropenic patients, HIV-infected patients, trauma patients, burn patients, patients with chronic or resistant infections such as those resulting from myelodysplastic syndrome, and the elderly, all of who may have weakened immune systems. An immunocompromised individual is generally defined as a person who exhibits an attenuated or reduced ability to mount a normal cellular and/or humoral defense to challenge by infectious agents, e.g., viruses, bacteria, fungi and protozoa. A protein malnourished individual is generally defined as a person who has a serum albumin level of less than about 3.2 grams per deciliter (g/dl) and/or unintentional weight loss of greater than 10% of usual body weight.

More particularly, the method of the invention can be used to therapeutically or prophylactically treat animals or humans who are at a heightened risk of infection due to imminent surgery, injury, illness, radiation or chemotherapy, or other condition which deleteriously affects the immune system. The method is useful to treat patients who have a disease or disorder which causes the normal metabolic immune response to be reduced or depressed, such as HIV infection (AIDS). For example, the method can be used to pre-initiate the metabolic immune response in patients who are undergoing chemotherapy or radiation therapy, or who are at a heightened risk for developing secondary infections or post-operative complications because of a disease, disorder or treatment resulting in a reduced ability to mobilize the body's normal metabolic responses to infection. Treatment with the neutral soluble glucans has been shown to be particularly effective in mobilizing the host's normal immune defenses, thereby engendering a measure of protection from infection in the treated host.

The present composition is generally administered to an animal or a human in an amount sufficient to produce immune system enhancement. The mode of administration of the neutral soluble glucan can be oral, enteral, parenteral, intravenous, subcutaneous, intraperitoneal, intramuscular, topical or intranasal. The form in which the composition will be administered (e.g., powder, tablet, capsule, solution, emulsion) will depend upon the route by which it is administered. The quantity of the composition to be administered will be determined on an individual basis, and will be based at least in part on consideration of the severity of infection or injury in the patient, the patient's condition or overall health, the patient's weight and the time available before surgery, chemotherapy or other high-risk treatment. In general, a single dose will preferably contain approximately 0.01 to approximately 10 mg of modified glucan per kilogram of body weight, and preferably from about 0.1 to 2.5 mg/kg. The dosage for topical application will depend upon the particular wound to be treated, the degree of infection and severity of the wound. A typical dosage for wounds will be from about 0.001 mg/ml to about 2 mg/ml, and preferably from about 0.01 to about 0.5 mg/ml.

In general, the compositions of the present invention can be administered to an individual periodically as necessary to stimulate the individual's immune response. An individual skilled in the medical arts will be able to determine the length of time during which the composition is administered and the dosage, depending upon the physical condition of the patient and the disease or disorder being treated. As stated above, the composition may also be used as a preventative treatment to pre-initiate the normal metabolic defenses which the body mobilizes against infections.

Neutral soluble β-glucan can be used for the prevention and treatment of infections caused by a broad spectrum of bacterial, fungal, viral and protozoan pathogens. The prophylactic administration of neutral soluble β-glucan to a person undergoing surgery, either preoperatively, intraoperatively and/or post-operatively, will reduce the incidence and severity of post-operative infections in both normal and high-risk patients. For example, in patients undergoing surgical procedures that are classified as contaminated or potentially contaminated (e.g., gastrointestinal surgery, hysterectomy, cesarean section, transurethral prostatectomy) and in patients in whom infection at the operative site would present a serious risk (e.g., prosthetic arthroplasty, cardiovascular surgery), concurrent initial therapy with an appropriate antibacterial agent and the present neutral soluble glucan preparation will reduce the incidence and severity of infectious complications.

In patients who are immunosuppressed, not only by disease (e.g., cancer, AIDS) but by courses of chemotherapy and/or radiotherapy, the prophylactic administration of the soluble glucan will reduce the incidence of infections caused by a broad spectrum of opportunistic pathogens including many unusual bacteria, fungi and viruses. Therapy using neutral soluble β-glucan has demonstrated a significant radio-protective effect with its ability to enhance and prolong macrophage function and regeneration and, as a result enhance resistance to microbial invasion and infection.

In high risk patients (e.g., over age 65, diabetics, patients having cancer, malnutrition, renal disease, emphysema, dehydration, restricted mobility, etc.) hospitalization frequently is associated with a high incidence of serious nosocomial infection. Treatment with neutral soluble β-glucan may be started empirically before catheterization, use of respirators, drainage tubes, intensive care units, prolonged hospitalizations, etc. to help prevent the infections that are commonly associated with these procedures. Concurrent therapy with antimicrobial agents and the neutral soluble β-glucan is indicated for the treatment of chronic, severe, refractory, complex and difficult to treat infections.

The compositions administered in the method of the present invention can optionally include other components, in addition to the neutral soluble β-glucan. The other components that can be included in a particular composition are determined primarily by the manner in which the composition is to be administered. For example, a composition to be administered orally in tablet form can include, in addition to neutral soluble β-glucan, a filler (e.g., lactose), a binder (e.g., carboxymethyl cellulose, gum arabic, gelatin), an adjuvant, a flavoring agent, a coloring agent and a coating material (e.g., wax or plasticizer). A composition to be administered in liquid form can include neutral soluble β-glucan and, optionally, an emulsifying agent, a flavoring agent and/or a coloring agent. A composition for parenteral administration can be mixed, dissolved or emulsified in water, sterile saline, PBS, dextrose or other biologically acceptable carrier. A composition for topical administration can be formulated into a gel, ointment, lotion, cream or other form in which the composition is capable of coating the site to be treated, e.g., wound site.

Compositions comprising neutral soluble glucan can also be administered topically to a wound site to stimulate and enhance wound healing and repair. Wounds due to ulcers, acne, viral infections, fungal infections or periodontal disease, among others, can be treated according to the methods of this invention to accelerate the healing process. Alternatively, the neutral soluble β-glucan can be injected into the wound or afflicted area. In addition to wound repair, the composition can be used to treat infection associated therewith or the causative agents that result in the wound. A composition for topical administration can be formulated into a gel, ointment, lotion, cream or other form in which the composition is capable of coating the site to be treated, e.g., wound site. The dosage for topical application will depend upon the particular wound to be treated, the degree of infection and severity of the wound. A typical dosage for wounds will be from about 0.01 mg/ml to about 2 mg/ml, and preferably from about 0.01 to about 0.5 mg/ml.

Another particular use of the compositions of this invention is for the treatment of myelodysplastic syndrome (MDS). MDS, frequently referred to as preleukemia syndrome, is a group of clonal hematopoietic stem cell disorders characterized by abnormal bone marrow differentiation and maturation leading to peripheral cytopenia with high probability of eventual leukemic conversion. Recurrent infection, hemorrhaging and erminal infection resulting in death typically accompany MDS. Thus, in order to reduce the severity of the disease and the frequency of infection, compositions comprising modified glucan can be chronically administered to a patient diagnosed as having MDS according to the methods of this invention, in order to specifically increase the infection fighting activity of the patient's white blood cells. Other bone marrow disorders, such as aplastic anemia (a condition of quantitatively reduced and defective hematopoiesis) can be treated to reduce infection and hemorrhage that are associated with this disease state.

Neutral soluble glucan produced by the present method enhances the non-specific defenses of mammalian mononuclear cells and significantly increases their ability to respond to an infectious challenge. The unique property of neutral soluble glucan macrophage activation is that it does not result in increased body temperatures (i.e., fever) as has been reported with many non-specific stimulants of those defenses. This critical advantage of neutral soluble glucan may lie in the natural profile of responses it mediates in white blood cells. It has been shown that the neutral soluble β-glucan of the present invention selectively activates immune responses but does not directly stimulate or prime cytokine (e.g., IL-1 and TNF) release from mononuclear cells, thus distinguishing the present neutral soluble glucan from other glucan preparations (e.g., lentinan, krestrn) and immunostimulants.

In addition, it has been demonstrated herein that the neutral soluble glucan preparation of the present invention possesses an unexpected platelet stimulating property. Although it was known that glucans have the ability to stimulate white blood cell hematopoiesis, the disclosed platelet stimulating property had not been reported or anticipated. This property can be exploited in a therapeutic regimen for use as an adjuvant in parallel with radiation or chemotherapy treatment. Radiation and chemotherapy are known to result in neutropenia (reduced polymorphonuclear (PMN) leukocyte cell count) and thrombocytopenia (reduced platelet count). At present, these conditions are treated by the administration of colony-stimulating factors such as GM-CSF and granulocyte colony-stimulating factor (G-CSF). Such factors are effective in overcoming neutropenia, but fail to impact upon thrombocytopenia. Thus, the platelet stimulating property of the neutral soluble glucan preparation of this invention can be used, for example, as a therapeutic agent to prevent or minimize the development of thrombocytopenia which limits the dose of the radiation or chemotherapeutic agent which is used to treat cancer.

The invention is further illustrated by the following Examples.

EXAMPLES

Example 1

PREPARATION OF NEUTRAL SOLUBLE GLUCAN FROM S. CEREVISIAE

Saccharomyces cerevisiae strain R4 Ad (a non-recombinant derivative of wild-type strain A364A), was grown in a large-scale fermentation culture using a defined glucose, ammonium sulfate minimal medium. The production culture was maintained under glucose limitation in a feed-batch mode (New Brunswick MPP80). When the growing culture reached late logarithmic phase, the fermentation was ended and the β-glucan was stabilized by adjusting the culture to pH 12±0.5 using 10M NaOH. The yeast cells containing β-glucan were harvested by continuous-flow centrifugation (Westfalia SA-1). After centrifugation, the cells were collected into a stainless steel extraction vessel.

The first step in the extraction process was an alkaline extraction accomplished by mixing the cells with 1M sodium hydroxide (NaOH) at 90°±5° C. for 1 hour. Upon completion of this alkaline extraction, the β-glucan remained in the solid phase, which was collected by continuous centrifugation (Westfalia SA-1). The collected cell wall fraction was extracted a second time using the same procedure and under the same conditions. Treatment with alkali hydrolyzed and solubilized the cellular proteins, nucleic acids, mannans, soluble glucans and polar lipids into the supernatant fraction, and deacetylated chitin to chitosan in the cell wall.

The second step in the extraction process was a pH 4.5±0.05 (adjusted with concentrated HCl) extraction at 75°±5° C. for 1 hour. This was followed by a 0.1M acetic acid extraction to complete the removal of glycogen, chitin, chitosan and remaining proteins. The solids were collected and rinsed twice with Purified Water USP to remove any residual acid as well as any yeast degradation products.

The third step in the extraction process was a set of six organic extractions. The first four extractions were carried out in isopropanol. The solids were collected by centrifugation and then subjected to two acetone extractions. The two-stage organic extractions eliminated nonpolar lipids and hydrophobic proteins which may have co-purified with the drug substance. The resulting wet solids were dried in a vacuum oven at 65°±5° C. for 48–96 hours to yield a free-flowing powder.

At this stage the extraction process yielded a stable, insoluble intermediate consisting of approximately 90% β-glucan, called whole glucan particles (WGPs). The dry WGP intermediate was stored at 15°–30° C. until further use.

The WGP powder was resuspended in 98% (w/v) formic acid, in a glass reaction vessel at room temperature. The resulting mixture was heated to 85°±5° C. for 20 minutes. Under these conditions, the WGPs were partially hydrolyzed and solubilized to provide the desired molecular weight distribution of soluble β-glucan which was then precipitated by adding 1.5 volumes of ethanol. After complete mixing, the preparation was centrifuged to collect the β-glucan precipitate. Any residual formic acid was removed by boiling the β-glucan preparation in Purified Water USP for three hours.

Any unhydrolyzed WGPs were then removed from the β-glucan solution by centrifugation. The β-glucan solution was raised to pH 12.5±0.5 by the addition of the concentrated sodium hydroxide. The remaining purification steps were carried out by ultrafiltration.

The soluble alkaline β-glucan preparation was passed through a 100,000 nominal molecular weight (NMW) cut-off membrane ultrafilter (Amicon DC10). Under alkaline conditions this membrane ultrafilter removed insoluble and high molecular weight soluble β-glucan. Trace low molecular weight degradation products were then removed by recirculation through a 10,000 NMW cut-off membrane ultrafilter. The ultrafiltration was conducted as a constant volume wash with 0.1M NaOH.

The β-glucan solution was re-annealed under controlled conditions by adjusting the pH to 7.0±0.5 with concentrated hydrochloric acid, heating to 60°±10° C., which was maintained for 20 minutes and then cooled. The neutral re-annealed solution was then concentrated and washed with Sodium Chloride Injection USP in a 70,000 NMW cut-off membrane ultrafilter (Filtron Minisep) to enrich for the re-annealed neutral soluble glucan. Next the material was filtered through a 300,000 NMW cut-off membrane ultrafilter (Filtron Minisep) to remove high molecular weight and aggregated glucan molecules. In the same ultrafilter, the neutral soluble glucan material was washed with Sodium Chloride Injection USP in a constant volume wash mode.

The neutral soluble glucan was then concentrated in a 10,000 NMW cut-off membrane ultrafilter. The concentration process continued until a concentration of at least 1.0 mg/ml hexose equivalent was achieved.

The resulting neutral soluble glucan was then subjected to filtration through a depyrogenating filter (0.1 micron Posidyne) and a sterile 0.2 micron filter (Millipak) to yield sterile, pyrogen-free neutral soluble glucan. The neutral soluble glucan solution was stored at controlled room temperature (15°–30° C.) until further use. The aqueous solubility of neutral soluble glucan in the pH range of 4 to 8 is approximately 100 mg/ml. The solubility increased with increasing pH and reached approx. 150 mg/ml at pH 13.

Example 2

ANALYSIS OF NEUTRAL SOLUBLE GLUCAN

A. Glucose, Mannose and Glucosamine

Monosaccharide analysis was performed to quantitate the relative amounts of β-glucan (as glucose), mannan or phosphomannan (as mannose), and chitin (as N-acetyl glucosamine) in the neutral soluble glucan. The sample was hydrolyzed to monosaccharides in 2M trifluoroacetic acid for 4 hours at 110° C., evaporated to dryness, and redissolved in water. Monosaccharides were separated on a Dionex HPLC system using a CarboPac PA100 column (4×250 mm) using 5M NaOH at 1 ml/min and quantitated using a pulsed electrochemical detector (Dionex Model PED-1). The sensitivity of this assay for monosaccharides is 0.1% (w/w).

Glucose (retention time of 16.6 min) was identified as the only monosaccharide component of neutral soluble glucan along with traces of glucose degradation products (from hydrolysis) anhydroglucose at 2.5 min and 5-hydroxymethylfurfural at 4.3 min. The results confirm that neutral soluble glucan consisted of ≧298% glucose.

B. FTIR

Fourier transform infrared spectroscopy by diffuse reflectance (FTIR, Matson Instruments, Polaris) of lyophilized neutral soluble glucan samples was used to determine the anomeric structure (α vs. β), and linkage type (β(1-3), β(1-6), β(1-4)) present in neutral soluble glucan. Absorption maxima of 890 $cm^{-1}$ identified β(1-3) linkages; 920 $cm^{-1}$ identified β(1-6) linkages. No presence of α-linked anomers (e.g., glycogen, 850 $cm^{-1}$) or β(1-4)-linked polysaccharides (e.g., chitin, 930 $cm^{-1}$) were detected.

Example 3

CONFORMATIONAL ANALYSIS

Figure 2:
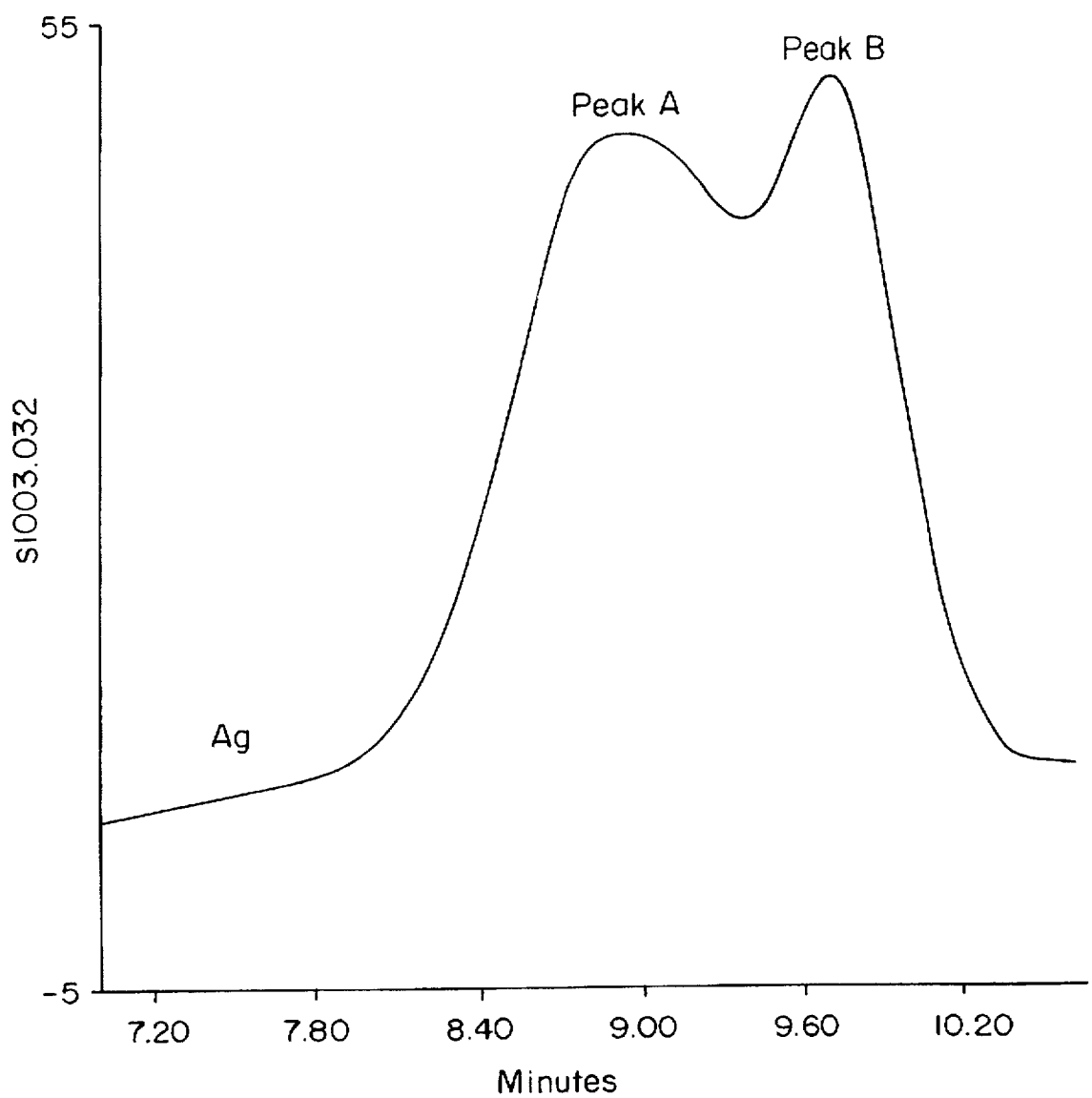
FIG. 2 shows a gel permeation chromatogram (pH 7) of soluble glucan which has not been purified by alkali dissociation and re-annealing. The chromatogram shows three species, referred to herein as high molecular weight aggregate (Ag), Peak A and Peak B (single helix glucan).
Figure 3:
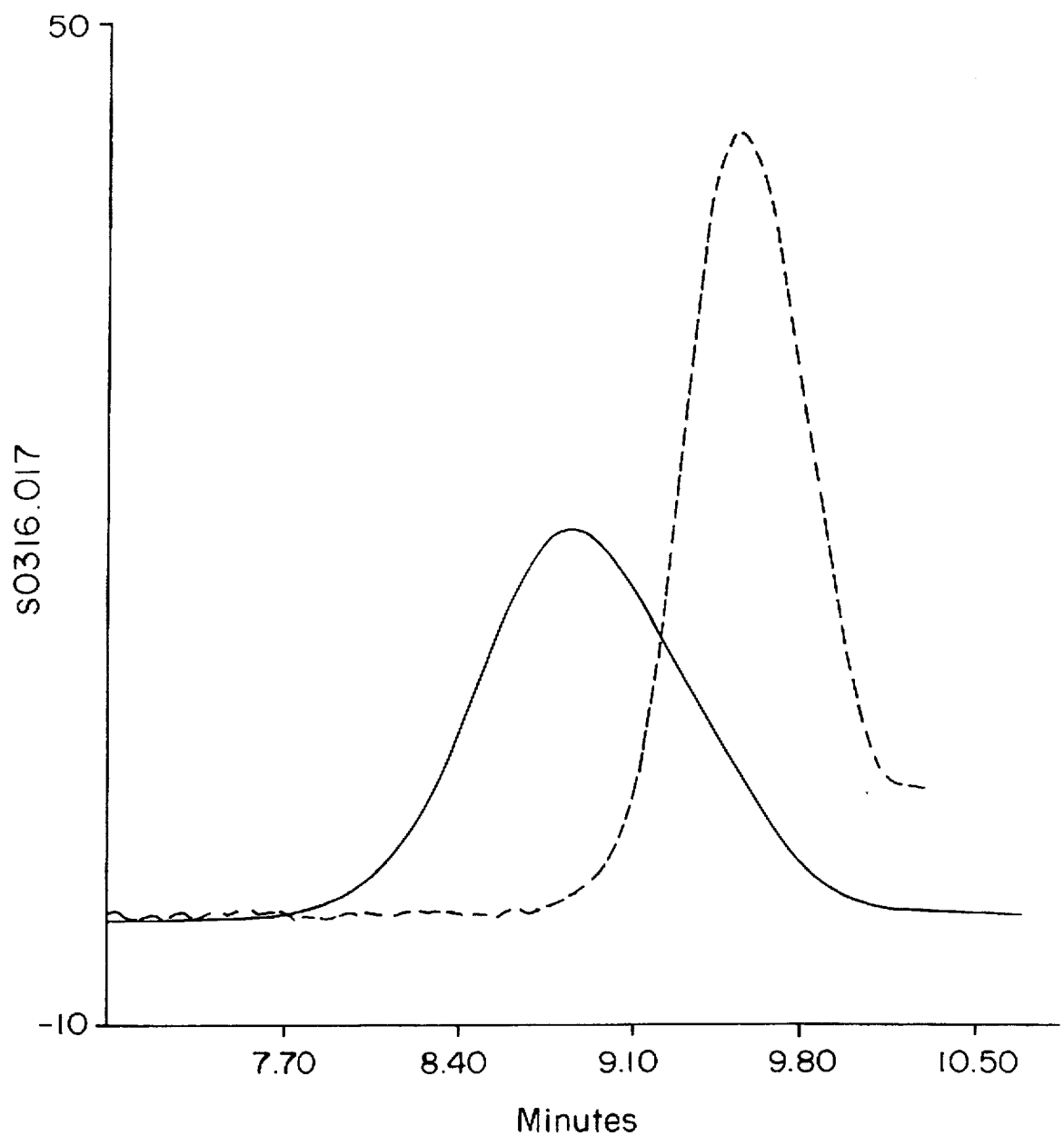
FIG. 3 is a chromatogram obtained for the neutral soluble glucan by gel permeation chromatography. The solid line represents the neutral soluble glucan at pH 7 and the broken line represents the neutral soluble glucan at pH 13.
Figure 4:
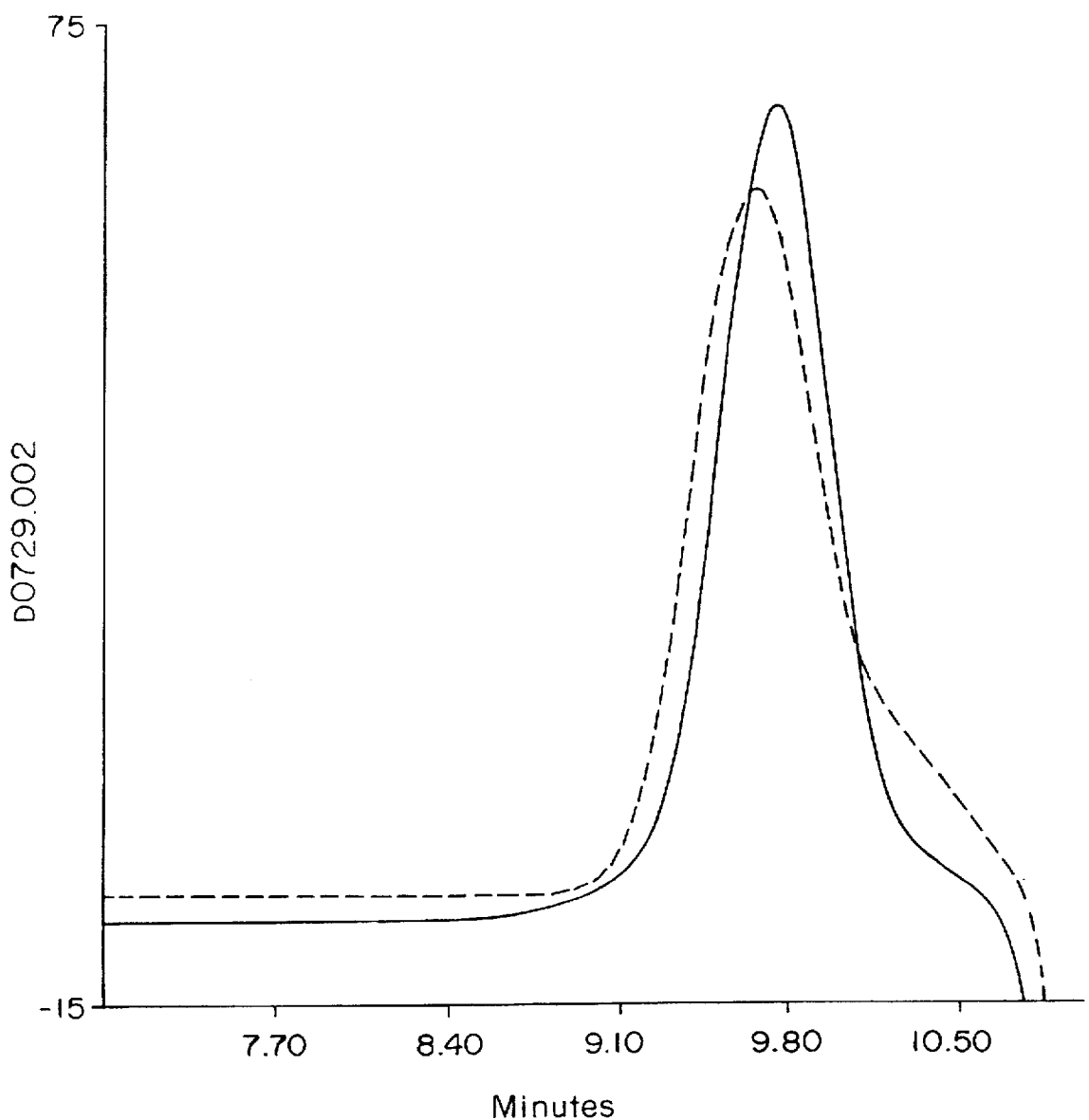
FIG. 4 is a chromatogram obtained for the single helix β-glucan (Peak B) by gel permeation chromatography. The solid line represents Peak B at pH 7 and the broken line represents Peak B at pH 13.

A solution of β-glucan which was not processed by alkali dissociation and re-annealing was analyzed for its compositional identity by gel permeation chromatography (pH 7) and found to contain multiple species, referred to herein as high molecular weight aggregate (Ag), Peak A and Peak B (See FIG. 2). Neutral soluble glucan which was prepared by alkali dissociation and re-annealing as described in Example 1, is present as a single peak (see FIG. 3) with an average molecular weight of 92,660 daltons at pH 7. The distinct conformations of neutral soluble glucan and Peak B were demonstrated by gel permeation chromatography at pH 7 and pH 13 using a refractive index detector. Neutral soluble glucan under-went a significant conformational transition from pH 7 to pH 13 which illustrates complete dissociation of the multiple helix at pH 7 to a single helical form at pH 13 (see FIG. 3). In contrast, Peak B only underwent a slight shift in molecular weight from pH 7 to pH 13 (see FIG. 4). The molecular weight of neutral soluble glucan and Peak B glucans as a function of pH is shown below in Table 1.

TABLE 1

| Sample | MW pH 7 | MW pH 13 | MW Ratio (pH 7/pH 13) |
|---|---|---|---|
| Neutral soluble glucan | 92,666 | 18,693 | 4.96 |
| Peak B | 8,317 | 7,168 | 1.16 |

The conformation of neutral soluble glucan and Peak B glucan was also determined by aniline blue complexing (Evans et al., 1984, Carb. Pol., 4:215–230; Adachi et al., 1988, Carb. Res., 177:91–100), using curdlan, a linear β(1-3) glucan, as the triple helix control and pustulan, a β(1-6) glucan, as a non-ordered conformational control. The results are discussed below and shown in Table 2.

The curdlan triple helix control complexed with aniline blue resulting in high fluorescence. Increasing the NaOH concentration began to dissociate the curdlan triple helix slightly, but NaOH concentrations >0.25M are required for complete dissociation of curdlan. The pustulan non-ordered control only formed a weak complex with aniline blue resulting in low fluorescence measurements which were not affected by NaOH concentration.

The neutral soluble glucan complexed effectively with aniline blue at low NaOH concentration (25 mM NaOH) resulting in high fluorescence. However, the neutral soluble glucan conformation dissociated significantly (50%) at NaOH concentrations as low as 150 mM NaOH indicating that it exists as a unique conformation compared to naturally occurring β-glucans, such as laminarin and curdlan, which require significantly higher NaOH concentrations for dissociation to occur. Peak B formed a weak complex with aniline blue due to its single helical conformation.

TABLE 2

Conformational Analysis of Glucans by Aniline Blue Complexing

| Test Material | Fluorescence | | |
|---|---|---|---|
| | 25 mM NaOH | 100 mM NaOH | 150 mM NaOH |
| Blank | 0 | 2 | 0 |
| Curdlan β(1-3) glucan | 53.5 | 41.6 | 36 |
| Pustulan β(1-6) glucan | 9.8 | 8.3 | 8.0 |
| Neutral soluble glucan | 40 | 25.6 | 20.2 |
| Peak B | 12.4 | 6.2 | 4.1 |

Example 4
EFFECTS OF NEUTRAL SOLUBLE GLUCAN ON HUMAN MONOCYTE PRODUCTION OF TNFα

Human peripheral blood mononuclear cells were isolated (Janusz et al., (1987), J. Immunol., 138: 3897–3901) from normal citrated and dextran-treated blood, washed in Hank's balanced salt solution (HBSS), lacking calcium, magnesium, and phenol red, and purified by gradient centrifugation on cushions of Ficoll-Paque (Pharmacia Fine Chemicals, Piscataway, N.J.). The mononuclear cells were collected into HBSS, washed twice, resuspended in RPMI 1640 Medium (Gibco, Grand Island, N.Y.) containing 1% heat-inactivated autologous serum (56° C. for 30 min.), and counted on the Coulter counter.

For the preparation of monocyte monolayers, 1 ml of $2.2 \times 10^6$ mononuclear cells/ml was plated into wells of 24-well tissue culture plates (CoStar, Cambridge, Mass.), incubated for 1 hour at 37° C. in a humidified atmosphere of 5% $CO_2$, and washed three times with RPMI to remove nonadherent cells. A second 1 ml aliquot of $2.2 \times 10^6$ mononuclear cells/ml was layered into each well and incubated for 2 hours described above before removal of the nonadherent cells. By visual enumeration at 40× with an inverted phase microscope and a calibrated reticle, the number of adherent cells for 30 different donors was $0.77 \pm 0.20 \times 10^6$ per well (mean±SD). By morphology and nonspecific esterase staining, >95% of the adherent cells were monocytes.

Monocyte monolayers were incubated at 37° C. in the $CO_2$ chamber for 0 to 8 hours with 0.5 ml of RPMI, 1% heat-inactivated autologous serum, 10 mM HEPES, and 5 mM $MgCl_2$ in the absence and presence of various glucan preparations. The culture supernatant was removed, clarified by centrifugation at 14,000 g for 5 min at 4° C., and stored at −70° C. before assay of TNFα.

The concentration of TNFα in the monocyte supernatants was measured by an enzyme-linked immunoadsorbent assay (ELISA) with the BIOKINE TNF Test kit (T Cell Sciences, Cambridge, Mass.), which had a lower limit of detectability of 40 pg/ml. The data are expressed as pg per $10^6$ monocytes, which was calculated by dividing the quantity of cytokine in 0.5 ml of supernatant by the number of monocytes per well.

For the determination of cell-associated levels of TNFα, the adherent monocytes were lysed in 0.25 ml PBS by three rounds of freezing and thawing, the lysates were cleared of debris by centrifugation at 14,000 g for 5 min at 4° C., and the resulting supernatants were stored at −70° C. Newly prepared monocyte monolayers contained no detectable levels of intracellular TNFα.

The results are shown in Tables 3 and 4 below.

TABLE 3

TNFα Synthesis by Human Monocytes Stimulated with Various Glucan Preparations

| Glucan | Conc. | TNFα ($pg/10^6$ monocytes) | | | |
|---|---|---|---|---|---|
| | | 1 | 2 | 3 | Mean ± SD |
| Buffer Control | | 36 | 39 | 2 | 26 ± 21 |
| Neutral soluble glucan | 1 mg/ml | 44 | 51 | 33 | 43 ± 9 |
| Laminarin | 1 mg/ml | 372 | 324 | 227 | 308 ± 74 |
| Whole Glucan particles | $4 \times 10^7$/ml | 2129 | 1478 | 1683 | 1763 ± 333 |

TABLE 4

TNFα Stimulation by Different Conformational Structures of Soluble β-Glucan

| Glucan | Conc. | TNFα ($pg/10^6$ monocytes) |
|---|---|---|
| Buffer Control | | 40 |
| Laminarin | 1 mg/ml | 1312 |
| Neutral soluble glucan | 1 mg/ml | 16 |
| Peak B | 1 mg/ml | 1341 |
| Glucan Particles | $4 \times 10^7$/ml | 2065 |

Table 3 shows that TNFα was stimulated by insoluble glucan particles and by laminarin, a soluble β(1-6) and β(1-3) linked glucan. There was no stimulation of TNFα by neutral soluble glucan. Table 4 shows similar results, but further confirms that TNFα stimulation is dependent upon conformational structure. The neutral soluble glucan did not stimulate TNFα while Peak B (single helical conformation) did stimulate TNFα.

Example 5
AVIDITY OF NEUTRAL SOLUBLE GLUCAN FOR THE GLUCAN RECEPTOR

Monolayers of human monocytes, prepared on siliconized glass coverslips (Czop et al., 1978, *J. Immunol.*, 120:1132), were incubated for 18 minutes at 37° C. in a humidified 5% $CO_2$ incubator with either 0.25 ml of buffer (RPMI-Mg-HEPES) or a range of concentrations (0.1–50 µg/ml) of neutral soluble glucan. The monocyte monolayers were then washed twice with 50 ml of RPMI 1640 medium and were layered with 0.25 ml of $4.8 \times 10^6$/ml zymosan particles (Czop and Austen, 1985, *J. Immunol.*, 14:2588–2593). After a 30 minute incubation at 37° C., the monolayers were washed three times with 50 ml of Hank's balanced salt solution to remove noningested zymosan particles. The monolayers were then fixed and stained with Giemsa. The ingestion of zymosan particles by at least 300 monocytes per monolayer was determined by visual observation under a 1000× light microscope.

Monocyte monolayers pretreated with buffer, 50 or 500 µg/ml of neutral soluble glucan as described above were subsequently tested for their capacity to ingest IgG coated sheep erythrocytes ($E^aIgG$). After an 18 minute preincubation with the neutral soluble glucan, the monolayers were incubated with 0.25 ml of $1 \times 10^7$/ml $E^aIgG$ for 30 minutes at 37° C., washed three times with 50 ml of Hank's balanced salt solution, treated for 4 minutes with 0.84% $NH_4Cl$ to lyse noningested $E^aIgG$, and fixed and stained as described above. The percentages of monocytes ingesting >1 and >3 $E^aIgG$ were determined by counting at least 300 monocytes per monolayer.

The percent inhibition of monocyte ingestion was determined by subtracting the percentage of monocytes ingesting targets after pretreatment with the neutral soluble glucan from the percentage ingesting targets after pretreatment with buffer, dividing this number by the percentage ingesting targets after pretreatment with buffer and multiplying by 100. The data are expressed as the mean of two experiments and are reported in Table 5.

TABLE 5

Glucan-receptor Binding Capacity of
Distinct Conformations of Soluble β-glucans

| Test Material | Conc. | % Inhibition |
|---|---|---|
| Buffer | — | 0% |
| Neutral soluble glucan | 50 µg/ml | 74% |
| | 500 µg/ml | 86% |
| Peak B | 50 µg/ml | 50% |
| | 500 µg/ml | 56% |

Both β-glucan preparations tested above inhibited monocyte ingestion of zymosan particles demonstrating their capacity to competitively bind to the β-glucan receptor on human monocytes. Neutral soluble glucan demonstrated a higher receptor binding capacity than Peak B as indicated by the greater level of inhibition achieved at both 50 µg/ml and 500 µg/ml. This biological assay demonstrates that the neutral soluble glucan is a superior ligand for the β-glucan receptor.

Example 6
LACK OF IN VITRO STIMULATION OF IL-1β AND TNFα FROM HUMAN MONONUCLEAR CELLS Venous blood was obtained from healthy male volunteers and mononuclear cells were fractionated by Ficoll-Hypaque centrifugation. The mononuclear cells were washed, resuspended in endotoxin-free RPMI-1640 culture medium - ultrafiltered to remove endotoxins as described elsewhere (Dinarello et al., 1987, *J. Clin. Microbiol.* 25:1233–8)—at a concentration of $5 \times 10^6$ cells/ml and were aliquoted into 96-well microtiter plates (Endres et al., 1989, *N.E. J. Med.* 320:265–271). The cells were then incubated with either 1 ng/ml endotoxin (lipopolysaccharide, *E. coli* 055:B5, Sigma, St. Louis), or 10 to 1000 ng/ml β-glucan, at 37° C. for 24 hours in 5% $CO_2$ and then lysed by three freeze-thaw cycles (Endres et al., 1989, *N.E. J. Med.* 320:265–271). Synthesis of IL-1β and TNFα was determined by specific radioimmunoassays as described elsewhere (Lisi et al., 1987, *Lymph Res.* 6:229–244; Lonnemann et al., 1988, *Lymph. Res.* 7:75–84; Van der Meer et al., 1988, *J. Leukocyte Biol.* 43:216–223.

To determine if neutral soluble glucan could act as a priming agent for cytokine synthesis with endotoxin, a known cytokine stimulant, mononuclear cells were pre-incubated with 1, 10, and 1000 ng/ml of the neutral soluble glucan for 3 hours at 37° C. in 5% $CO_2$. The cells were washed to remove neutral soluble glucan and were then incubated with 1 ng/ml endotoxin as described above. IL-1β and TNFα were determined as described above.

The results are summarized in Table 6. Neutral soluble glucan used as a stimulant at doses of 10–1000 ng/ml alone did not induce increased levels of IL-1β or TNFα synthesis over the control buffer treated cells. Endotoxin LPS, a known stimulant, resulted in significantly increased levels of both cytokines. In a second phase of this experiment neutral soluble glucan was tested for its ability to act as a priming agent for mononuclear cell cytokine synthesis. The cells from the same donors were pre-incubated with three doses of neutral soluble glucan (10–1000 ng/ml) and were then exposed to endotoxin as a co-stimulant. Neutral soluble glucan did not result in any amplification of the IL-1β and TNFα levels compared to endotoxin alone.

TABLE 6

In Vitro IL-1β and TNFα Synthesis by
Human Peripheral Blood Mononuclear Cells

| Stimulant | | IL-1β (ng/ml)[1] | TNFα (ng/ml)[1] |
|---|---|---|---|
| Cells only | | <0.10 | 0.14 |
| Neutral soluble glucan | 10 ng/ml | 0.13 | 0.16 |
| | 100 ng/ml | 0.12 | 0.16 |
| | 1000 ng/ml | <0.10 | 0.14 |
| LPS | 1 ng/ml | 2.62 | 2.22 |
| LPS(1 ng/ml) + Neutral | 10 ng/ml | 2.62 | 2.25 |
| soluble | 100 ng/ml | 2.57 | 2.07 |
| glucan | 1000 ng/ml | 2.85 | 2.27 |

[1]Values are the mean of two donors.

Example 7
IN VIVO PROTECTION AGAINST INFECTION IN RATS

A sepsis model was developed in rats to characterize the efficacy of β-glucan in protecting an immunologically intact host against serious infections, such as those which commonly occur following abdominal surgery. The rat model for intra-abdominal sepsis has been well described in the scientific literature (Onderdonk et al., 1974, *Infect. Immun.*, 10:1256–1259).

Groups of rats received neutral soluble glucan (100 µg/0.2 ml) or saline control (0.2 ml) intramuscularly 24 hours and 4 hours prior to infectious challenge. A defined polymicrobic infectious challenge (cecal inoculum) was placed into a gelatin capsule which was then surgically implanted into the peritoneal cavity of anesthetized rats through an anterior midline incision. The early peritonitis from this experimentally induced infection was associated with the presence of gram-negative organisms within the blood and peritoneal cavity culminating in mortality. The cecal inoculum contained an array of facultative species, such *E. coli*, as well as other obligate anaerobes (*Streptococcus sp., Bacteroides sp., Clostridium perfringens, Clostridium ramosum, Peptostreptococcus magnus* and *productus, Proteus mirabilis*). The animals were observed four times per day for the first 48 h and twice per day thereafter. The results are reported in Table 7.

TABLE 7

Effect of Neutral Soluble Glucan on Mortality in a Rat Model for Intra-abdominal Sepsis

| Group | Mortality (%) | P vs. Saline |
|---|---|---|
| Saline | 12/20 (60) | |
| Neutral soluble glucan | 2/10 (10) | <0.01 |

These results demonstrate that neutral soluble glucan which does not induce IL-1β and TNFα protects rats from lethal bacterial challenge.

Example 8
DEMONSTRATION OF SAFETY FOR HUMAN ADMINISTRATION

Figure 5:
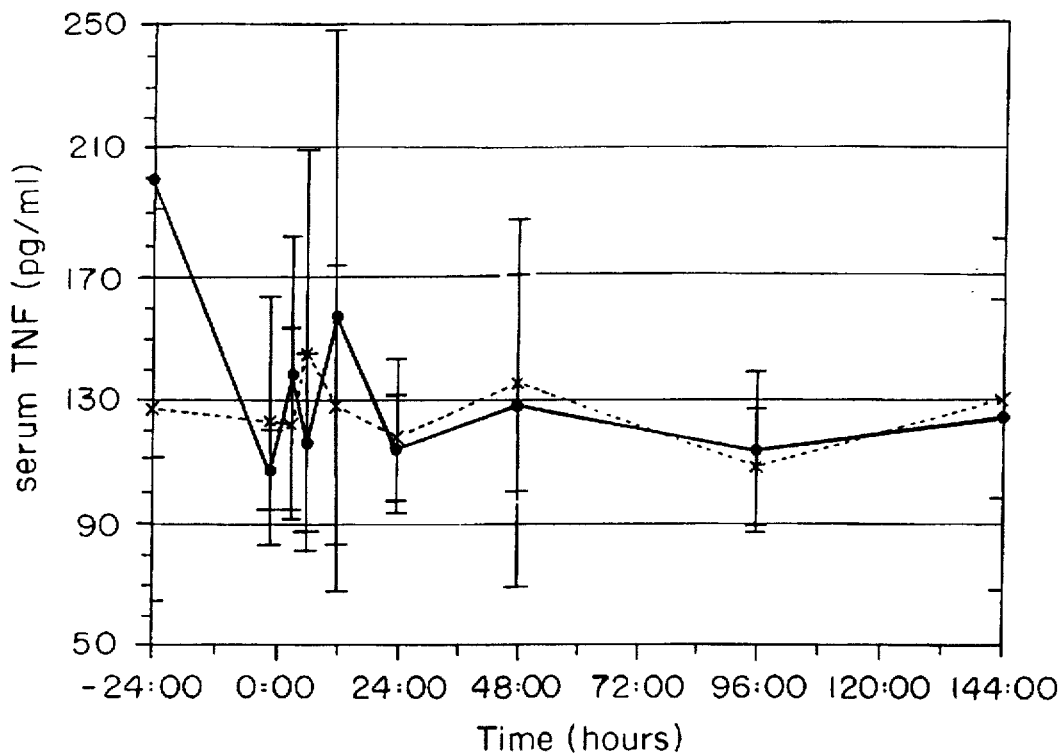
FIG. 5 shows the change in serum TNF levels, over time, taken from patients intravenously infused with placebo (broken line) or neutral soluble glucan (solid line).
Figure 6:
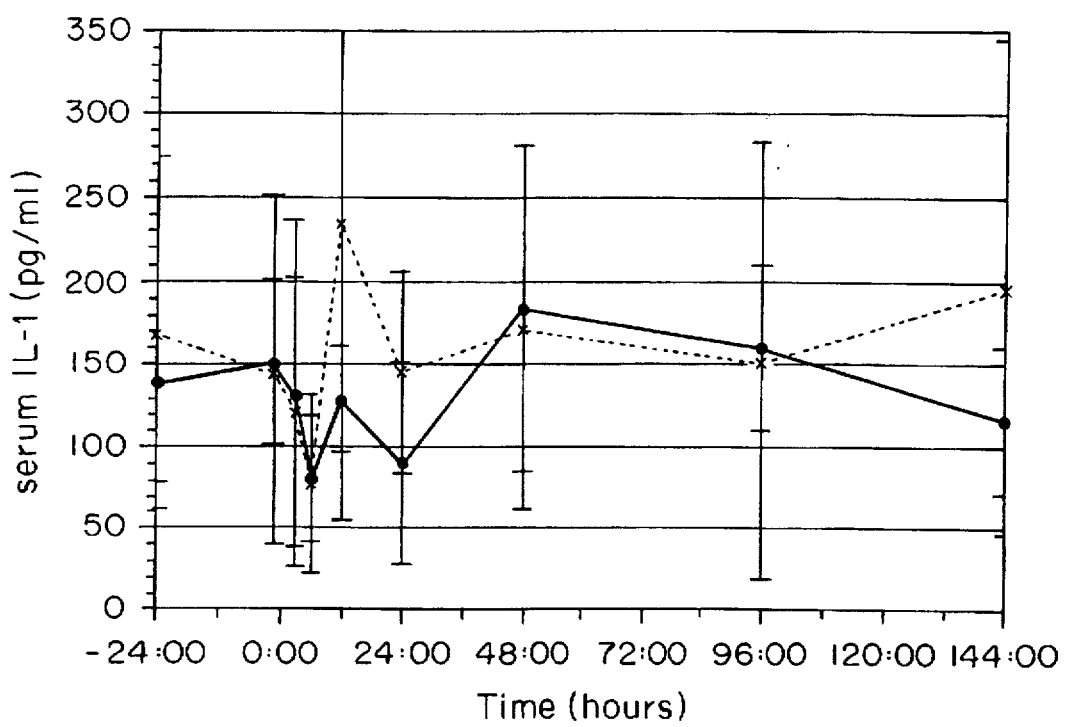
FIG. 6 shows the change in serum IL-1 levels, over time, taken from patients intravenously infused with placebo (broken line) or neutral soluble glucan (solid line).

A randomized, double-blind, placebo-controlled clinical trial was conducted on healthy males to evaluate the safety of neutral soluble glucan (2.25 mg/kg) injected by intravenous infusion compared to a placebo control. No adverse effects were observed. There was also no observed elevation in IL-1, TNF, IL-6, IL-8 and GM-CSF. Single intravenous administration of neutral soluble glucan resulted in an increase in monocytes and neutrophils and in the killing activity of these cells proving that neutral soluble glucan retains the desirable immunological activities in humans. See Tables 8, 9 and 10 below. However, as shown in FIGS. 5 and 6 no changes occurred in serum IL-1 and TNF and none of the patients experienced fever or inflammatory reactions. The results are consistent with the in vitro data reported in the earlier examples.

TABLE 8

Change In Absolute Neutraphil Counts (×1000/μl) After Neutral Soluble Glucan Administration

| Dose Level | | B | Hour 8 | Hour 12 | Hour 24 |
|---|---|---|---|---|---|
| Saline | Mean | 4.06 | 4.34 | 4.31 | 3.43 |
| | SD | 2.12 | 1.53 | 1.16 | 1.46 |
| | N | 6 | 6 | 6 | 6 |
| 2.5 mg/kg | Mean | 4.11 | 11.29* | 8.18 | 5.32 |
| Neutral | SD | 1.15 | 4.39 | 3.80 | 1.75 |
| Soluble Glucan | N | 6 | 6 | 6 | 6 |

B = Baseline measurement
*p < 0.01 with respect to baseline

TABLE 9

Change in Monocte Counts (×1000/μl) After Neutral Soluble Glucan Administration

| Dose Level | | B | Hour 8 | Hour 12 | Hour 24 |
|---|---|---|---|---|---|
| Saline | Mean | 0.33 | 0.44 | 0.59 | 0.33 |
| | SD | 0.09 | 0.10 | 0.22 | 0.12 |

TABLE 9-continued

Change in Monocte Counts (×1000/μl) After Neutral Soluble Glucan Administration

| Dose Level | | B | Hour 8 | Hour 12 | Hour 24 |
|---|---|---|---|---|---|
| | N | 6 | 6 | 6 | 6 |
| 2.5 mg/kg | Mean | 0.24 | 0.63* | 0.67* | 0.31 |
| Neutral | SD | 0.10 | 0.24 | 0.32 | 0.15 |
| Soluble Glucan | N | 6 | 6 | 6 | 6 |

B = Baseline measurement
*p < 0.01 with respect to baseline

TABLE 10

Ex Vivo Microbicidal Activity of Normal Volunteers Receiving Neutral Soluble Glucan Mean Change in % Killing[1]

| Dose Level | | Hour 3 | Hour 6 | Hour 24 | Day 2 | Day 3 | Day 6 |
|---|---|---|---|---|---|---|---|
| Saline | | 0 | 0 | 0 | 0 | 0 | 0 |
| 2.5 mg/kg | Mean | 42.86 | 32.33 | 20.90 | 48.96 | 39.22 | 31.17 |
| Neutral | N | 6 | 6 | 6 | 6 | 6 | 6 |
| Soluble Glucan | p-Value | 0.062 | 0.036 | 0.300 | 0.045 | 0.085 | 0.026 |

[1]Normalized with respect to the saline control

Example 9
DEMONSTRATION OF EFFICACY IN VIVO AS HUMAN ANTI-INFECTIVE

In this clinical study, the safety, tolerance, and potential efficacy of the neutral soluble β-glucan was evaluated in patients undergoing major thoracoabdominal surgery with high risk of post-operative infection. Thirty-four males and females who underwent surgery received 0.5 mg/kg of the neutral soluble β-glucan preparation or saline placebo, given as an intravenous infusion of 50 to 200 ml over one hour. Patients received multiple sequential doses of the neutral soluble β-glucan or placebo at 12 to 24 hours prior to surgery, 1 to 4 hours prior to surgery, 48 hours post-surgery, and 96 hours post-surgery.

Hospitalization, infections, and usage of anti-infective medications were examined as potential clinical efficacy parameters. Compared to patients given saline placebo infusions, patients who received the neutral soluble β-glucan spent an average of five fewer days in the hospital (12.3±6.1 days versus 17.3±15.5 days) and three fewer days in the Intensive Care Unit (0.1±0.4 versus 3.3±6.3 days; p<0.03, one-way analysis of variance).

The number of anti-infective medication prescriptions written per study day following surgery was consistently higher for control patients than for β-glucan recipient patients. Control patients were prescribed an average of three times the number of anti-infective medications as β-glucan recipients over the time period from surgery to discharge (p<0.005). During the Treatment and Post-Treatment Follow-up Phases, a total of 22 culture-confirmed infections in 5 control patients and 8 infections in 5 β-glucan recipient patients were identified (p<0.002).

Neutrophils (PMNs) and monocytes/macrophages (MOs) were purified from blood samples obtained at Baseline, Day 1, and Day 5 and examined for basal and phorbol myrisate acetate stimulated microbicidal activity against *Staphylococcus aureus, Escherichia coli* and *Candida albicans*. The neutral soluble β-glucan treatment generally increased the basal and phorbol-induced microbicidal activity of MOs and PMNs.

Example 10
WOUND HEALING EFFECTS OF NEUTRAL SOLUBLE GLUCANS

Wound healing studies were performed in a hairless mouse model having full thickness wounds with and without *Staphylococcus aureus* infection. Hairless SKH-1 inbred mice (6–8 weeks of age) were anesthetized with ether and a midline 3 cm full thickness longitudinal incision was made with a number 10 scalpel blade, producing a full thickness wound that did not penetrate the underlying fascia. Incisions were closed using steel clips placed at 1 cm intervals.

Formulations of neutral soluble glucan in phosphate buffered saline were applied 30 minutes following wounding and reapplied at 24 hour intervals during the seven day post-operative period. Two micrograms of neutral soluble glucan/mouse per day was topically applied. Wounds were examined daily and rank-ordered for effectiveness of formulation for enhancement of visual based wound healing. Wounds were scored for closure on a scale of 0–5, with 5 indicating the most healing. In one group of mice infected, the wound was treated with a culture of $10^7$ *Stanhvlococcus aureus* 30 minutes after wounding and 2 hrs prior to treatment with the neutral soluble glucan formulation.

Histological evaluation of the wound site of each test group was made. The dermis of the control group (untreated wound) was heavily infiltrated with both lymphocytes and monocytes/macrophages. However, reepithelialization that occurred at the epidermal layer was incomplete. The tissue section showed that the dermal tissue was weak, in that the tissue integrity was not maintained when it was sectioned.

The histology of the wounded tissue isolated from mice treated for three days with phosphate buffered saline containing the neutral soluble glucan showed that there was a heavy infiltration of macrophages and lymphocytes. Tissue integrity was good.

When topically applied to a wound, a composition of neutral soluble glucan stimulated white blood cell entry and activity at the wound site and accelerated wound healing within the dermal layer of the wound. Furthermore, the composition effectively eliminated infection produced by bacterial infection (*S. aureus*) and prevented the progression to sepsis. Untreated wounds progressed to sepsis.

Example 11
STIMULATION OF PLATELET PROLIFERATION BY NEUTRAL SOLUBLE GLUCAN The platelet proliferation stimulatory effect of the neutral soluble glucan was tested in an animal model system following either irradiation or administration of the chemotherapeutic agent cisplatin. These experiments demonstrated the unexpected platelet stimulatory effect.

Figure 7:
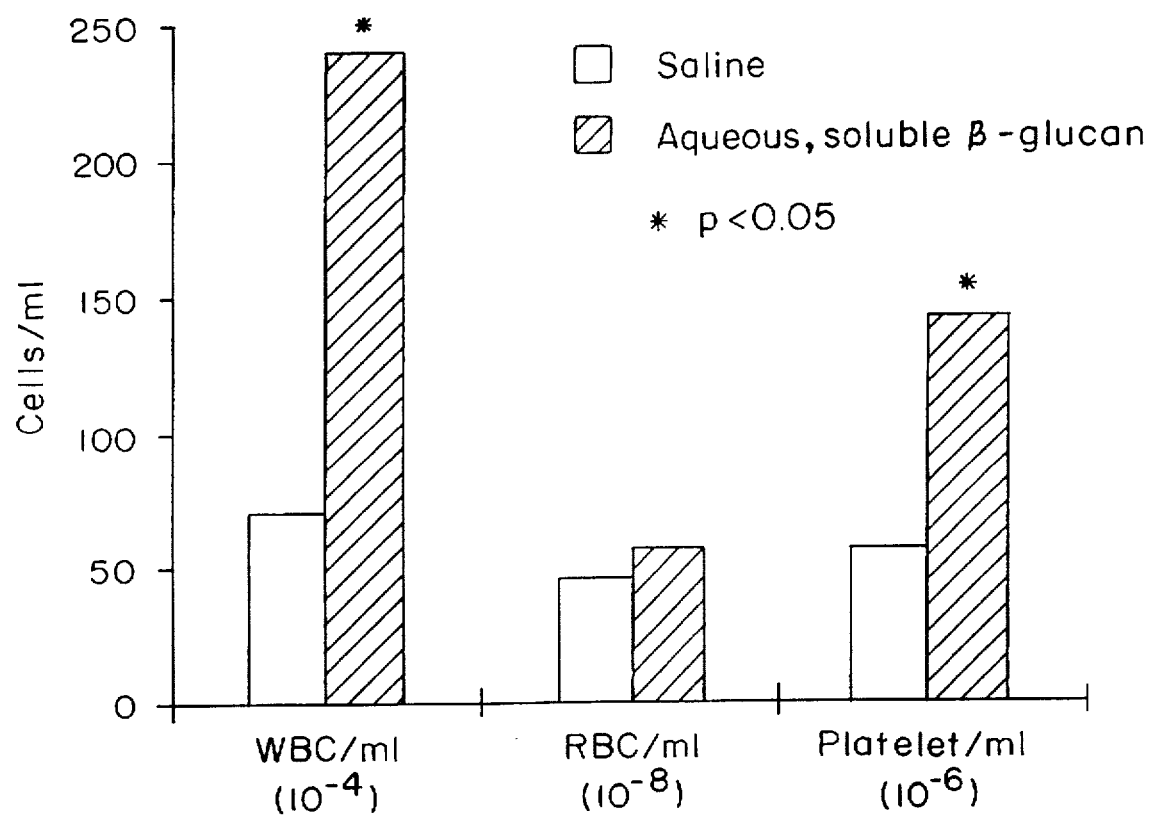
FIG. 7 is a diagram representing peripheral blood counts from irradiated mice following administration of neutral soluble glucan.

More specifically, saline or neutral soluble glucan prepared as described in Example 1 was administered to groups of 10 mice as a single IV bolus 20 hours prior to radiation exposure. Mice were bilaterally exposed to a total-body irradiation of 7.5-Gy. Fourteen days after irradiation the mice were sacrificed and whole blood samples were analyzed for peripheral blood counts. As shown in FIG. 7, the platelet cell count from neutral soluble glucan-treated mice was increased nearly 3-fold relative to saline-treated control levels.

Figure 8:
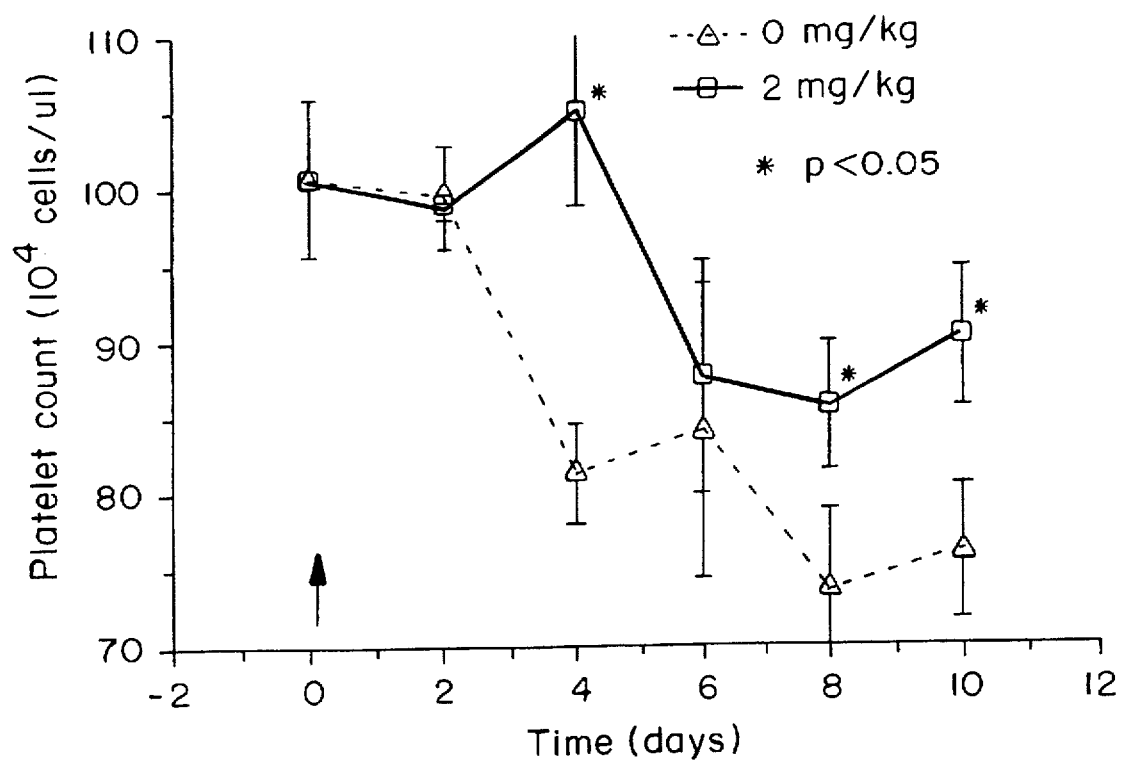
FIG. 8 is a diagram representing platelet cell counts from cisplatin-treated mice following administration of neutral soluble glucan.

In addition to tests on irradiated mice, cisplatin-treated mice were also tested for the effect of the neutral soluble glucan on platelet hematopoiesis. Balb/c mice were injected intravenously with cisplatin at a dose of 9.3 mg/kg through the tail vein one hour before injecting either saline or the neutral soluble glucan, prepared as described in Example 1, intramuscularly in a single dose of 0 (saline) or 2 mg/kg on Day 0. Platelet counts were determined before treatment (Day 0) and at 2, 4, 6, 8, and 10 days post-treatment. The results of this experiment are shown in FIG. 8. Each data point represents the mean and standard error of platelet counts from five mice. The statistically significant differences ($p<0.05$) between the saline and neutral soluble glucan (2 mg/kg) are noted.

Biological Deposit

*Saccharomyces cerevisiae* strain R4 Ad was deposited on Aug. 20, 1992 with the American Type Culture Collection (ATCC), 12301 Parklawn Drive, Rockville, Maryland, under the terms of the Budapest Treaty. The strain has been assigned ATCC accession number 74181. Upon issuance of a patent, this deposit will be irrevocable.

Equivalents

Those skilled in the art will recognize or be able to ascertain, using no more than routine experimentation, many equivalents to the specific materials and components described herein. Such equivalents are intended to be encompassed in the scope of the following claims:

We claim:

1. A method for inducing an immune response in an animal or human, comprising administering to the animal or human an underivatized, aqueous soluble β(1-3)-glucan in a triple helix conformation having immunostimulating properties, which does not stimulate or prime the production of interleukin-1 or tumor necrosis factor or both, in virro, in an amount sufficient to induce an immune system response.

2. The method of claim 1 wherein the β(1-3) glucan is derived from yeast.

3. The method of claim 2 wherein the yeast is a strain of *Saccharomyces cerevisiae*.

4. The method of claim 3 wherein *Saccharonmyces cerevisiae* is strain R4 (NRRL Y-15903) or strain R4 Ad (ATCC 74181).

5. A method of claim 1 in which the animal or human is injured, immunocoapromised, protein-malnourished, elderly, neutropenic, burned, facing imminent surgery, preparing to undergo chemo-therapy, radiation therapy, bone marrow transplant or dialysis or has myelodysplastic syndrome.

6. The method of claim 1 in which the β(1-3)-glucan is administered orally or parenterally.

7. The method of claim 6 wherein the mode of administration of the glucan is a parenteral mode selected from the group consisting of intravenous, subcutaneous, intramuscular and intraperitoneal administration.

8. A method for preventing infection in an animal or human that is at risk for infection, comprising administering to the animal or human an underivatized, aqueous soluble β(1-3) glucan in a triple helix conformation having immunostimulating properties, which does not stimulate or prime the production of interleukin-1, tumor necrosis factor or both, in vitro, in an amount sufficient to prevent infection.

9. The method of claim 8 wherein the β(1-3) glucan is derived from yeast.

10. The method of claim 9 wherein the yeast is a strain of *Saccharomyces cerevisiae*.

11. The method of claim 10 wherein *Sacchxromyces cerevisiae* is strain R4 (NRRL Y-15903) or strain R4 Ad (ATCC 74181).

12. The method of claim 8 wherein the infection is caused by bacterial, viral, fungal or protozoan agents.

13. A method of claim 8 in which the animal or human is injured, immunocompromised, protein-malnourished, elderly, neutropenic, burned, facing imminent surgery, preparing to undergo chemo-therapy, radiation therapy, bone marrow transplant or dialysis or has myelodysplastic syndrome.

14. A method of claim 8 in which the β(1-3)-glucan is administered orally or parenterally.

15. A method of claim 14 wherein the mode of administration of the glucan is a parenteral mode selected from the group consisting of intravenous, subcutaneous, intramuscular and intraperitoneal administration.

16. The method of claim 8 further comprising administering an antimicrobial agent to the animal or human.

17. A method for treating infection in an animal or human that is at risk of infection, comprising administering to the animal or human an underivatized, aqueous soluble β(1-3)-glucan in a triple helix conformation having immunostimulating properties, which does not stimulate or prime the production of interleukin-1 or tumor necrosis factor or both, in vitro, in an amount sufficient to reduce infection.

18. The method of claim 17 in which the animal or human is injured, immunocompromised, protein-malnourished, elderly, neutropenic, burned, facing imminent surgery, preparing to undergo chemo-therapy, radiation therapy, bone marrow transplant or dialysis or has myelodysplastic syndrome.

19. The method of claim 17 in which the β(1-3)-glucan is administered orally or parenterally.

20. The method of claim 19 wherein the mode of administration of the glucan is a parenteral mode selected from the group consisting of intravenous, subcutaneous, intramuscular and intraperitoneal administration.

21. The method of claim 17 wherein the infection is caused by bacterial, viral, fungal or protozoan agents.

22. The method of claim 17 wherein the β(1-3) glucan is derived from yeast.

23. The method of claim 22 wherein the yeast is a strain of *Sacchaxomyces cerevisiae*.

24. The method of claim 23 wherein *Saccharomyces cerevisiae* is strain R4 (NRRL Y-15903) or strain R4 Ad (ATCC 74181).

25. The method of claim 17 further comprising administering an antimicrobial agent to the animal or human.

26. A method for stimulating repair and healing of a wound site on an animal or human comprising administering to the wound site, an underivatized, aqueous soluble β(1-3)-glucan in a triple helix conformation having immunostimulating properties, which does not stimulate or prime the production of the interleukin-1 or tumor necrosis factor or both, in vitro, in an amount sufficient to stimulate repair and healing of the wound site.

27. The method of claim 26 wherein the β(1-3) glucan is derived from yeast.

28. The method of claim 27 wherein the yeast is a strain of *Saccharomyces cerevisiae*.

29. The method of claim 28 wherein *Saccharoznyces cerevisiae* is strain R4 (NRRL Y-15903) or strain R4 Ad (ATCC 74181).

30. The method of claim 26 wherein the β(1-3) glucan is topically administered to the wound site or is injected into the wound site.

31. The method of claim 26 further comprising administering an antimicrobial agent to the animal or human.

32. A method for stimulating wound healing and healing of infection associated therewith, comprising administering to the wound site, an underivatized, aqueous soluble β(1-3)-glucan in a triple helix conformation having immunostimulating properties, which does not stimulate or prime the production of interleukin-1 or tumor necrosis factor or both, in vitro in an amount sufficient for stimulating wound healing and healing of infection.

33. The method of claim 32 wherein the β(1-3) glucan is derived from yeast.

34. The method of claim 33, wherein the yeast is a strain of *Saccharomyces cerevisiae*.

35. The method of claim 34 wherein *Saccharomyces cerevisiae* is strain R4 (NRRL Y-15903) or strain R4 Ad (ATCC 74181).

36. The method of claim 32 wherein the β(1-3) glucan is topically administered to the wound site or injected into the wound site.

37. The method of claim 32 wherein the infection is caused by bacterial, viral, fungal or protozoan agents.

38. The method of claim 32 further comprising administering an antimicrobial agent to the animal or human.

39. A method for enhancing the microbicidal activity of phagocytic cells comprising administering to an animal or human an underivatized, aqueous soluble β(1-3)-glucan in a triple helix conformation having immunostimulating properties, which does nor stimulate or prime the production of inter-leukin-1 or tumor necrosis factor or both, in vitro, in an amount sufficient for enhancing microbicidal activity of phagocytic cells.

40. The method of claim 39 wherein the β(1-3) glucan is derived from yeast.

41. The method of claim 40, wherein the yeast is a strain of *Saccharomyces cerevisiae*.

42. The method of claim 41 wherein *Saccharomyces cerevisiae* is strain R4 (NRRL Y-15903) or strain R4 Ad (ATCC 74181).

43. The method claim 39 wherein the β(1-3) glucan is administered orally or parenterally.

44. The method of claim 43 wherein the mode of administration is a parenteral mode selected from the group consisting of intravenous, subcutaneous, intramuscular and intraperitoneal administration.

45. A method for stimulating hematopoiesis comprising administering to an animal or human an underivatized, aqueous soluble β(1-3)-glucan in a triple helix conformation having immunostimulating properties, which does not stimulate or prime the production of interleukin-1 or tumor necrosis factor or both, in vitro in an amount sufficient for stimulating hematopoiesis.

46. The method of claim 45 wherein the β(1-3) glucan is derived from yeast.

47. The method of claim 46, wherein the yeast is a strain of *Saccharomyces cerevisiae*.

48. The method of claim 47 wherein *Saccharomyces cerevisiae* is strain R4 (NRRL Y-15903) or strain R4 Ad (ATCC 74181).

49. A method of claim 45 in which the β-glucan is administered orally or parenterally.

50. A method of claim 49 wherein the mode of administration of the glucan is a parenteral mode selected from the group consisting of intravenous, subcutaneous, intramuscular and intraperitoneal administration.

51. A method for stimulating the proliferation of monocytes and neutrophils in an animal or human, comprising administering to the animal or human an underivatized, aqueous soluble β(1-3)-glucan in a triple helix conformation having immuno-stimulating properties, which does not stimulate or prime the production of interleukin-1 or tumor necrosis factor or both, in vitro, in an amount sufficient for stimulating proliferation of monocytes and neutrophils.

52. The method of claim 51 wherein the β(1-3) glucan is derived from yeast.

53. The method of claim 52, wherein the yeast is a strain of *Saccharomyces cerevisiae*.

54. The method of claim 53 wherein *Saccharomyces cerevisiae is strain R4* (NRRL Y-15903) or strain R4 Ad (ATCC 74181).

55. A method of claim 51 in which the β-glucan is administered orally or parenterally.

56. A method of claim 55 wherein the mode of administration of the glucan is a parenteral mode selected from the group consisting of intravenous, subcutaneous, intramuscular and intraperitoneal administration.

57. A method for treating refractory infections comprising administering to an animal or human an antimicrobial agent and an underivatized, aqueous soluble β(1-3)-glucan in a triple helix conformation having immunostimulating properties, which does not stimulate or prime the production of interleukin-1 or tumor necrosis factor, or both, in vitro.

58. A method for inducing an immune response in an animal or human, comprising administering to the animal or human an underivatized, aqueous soluble β(1-3)-glucan in a triple helix conformation, said glucan capable of enhancing immune response without stimulating production of biochemical mediators that cause inflammatory side effects, in an amount sufficient to induce an immune system response.

59. The method of claim 58 wherein the β(1-3) glucan is derived from yeast.

60. The method of claim 59 wherein the yeast is a strain of *Saccharomyces cerevisiae*.

61. A method for preventing infection in an animal or human that is at risk for infection, comprising administering to the animal or human an underivatized, aqueous soluble β(1-3) glucan in a triple helix conformation, said glucan capable of enhancing immune response without stimulating production of biochemical mediators that cause inflammatory side effects, in an amount sufficient to prevent infection.

62. The method of claim 61 wherein the β(1-3) glucan is derived from yeast.

63. The method of claim 62 wherein the yeast is a strain of *Saccharomyces cerevisiae*.

64. A method for treating infection in an animal or human that is at risk of infection, comprising administering to the animal or human an underivatized, aqueous soluble β(1-3)-glucan in a triple helix conformation, said glucan capable of enhancing immune response without stimulating production of biochemical mediators that cause inflammatory side effects, in an amount sufficient to reduce infection.

65. A method for stimulating repair and healing of a wound site on an animal or human comprising administering to the wound site, an underivatized, aqueous soluble β(1-3)-glucan in a triple helix conformation, said glucan capable of enhancing immune response without stimulating production of biochemical mediators that cause inflammatory side effects, in an amount sufficient to stimulate repair and healing of the wound site.

66. The method of claim 65 wherein the β(1-3) glucan is derived from yeast.

67. The method of claim 66 wherein the yeast is a strain of *Saccharomyces cerevisiae*.

68. A method for stimulating wound healing and healing of infection associated therewith, comprising administering to the wound site, an underivatized, aqueous soluble β(1-3)-glucan in a triple helix conformation, said glucan capable of enhancing immune response without stimulating production of biochemical mediators that cause inflammatory side effects, in an amount sufficient for stimulating wound healing and healing of infection.

69. The method of claim 68 wherein the β(1-3) glucan is derived from yeast.

70. The method of claim 69, wherein the yeast is a strain of *Saccharomyces cerevisiae*.

71. A method for enhancing the microbicidal activity of phagocytic cells comprising administering to an animal or human an underivatized, aqueous soluble β(1-3)-glucan in a triple helix conformation, said glucan capable of enhancing immune response without stimulating production of biochemical mediators that cause inflammatory side effects, in an amount sufficient for enhancing microbicidal activity of phagocytic cells.

72. The method of claim 71 wherein the β(1-3) glucan is derived from yeast.

73. The method of claim 72, wherein the yeast is a strain of *Saccharomyces cerevisiae*.

74. A method for stimulating hematopoiesis comprising administering to an animal or human an underivatized, aqueous soluble β(1-3)-glucan in a triple helix conformation, said glucan capable of enhancing immune response without stimulating production of biochemical mediators that cause inflammatory side effects, in an amount sufficient for stimulating hematopoiesis.

75. The method of claim 74 wherein the β(1-3) glucan is derived from yeast.

76. The method of claim 75, wherein the yeast is a strain of *Saccharomyces cerevisiae*.

77. A method for stimulating the proliferation of monocytes and neutrophils in an animal or human, comprising administering to the animal or human an underivatized, aqueous soluble β(1-3)-glucan in a triple helix conformation, said glucan capable of enhancing immune response without stimulating production of biochemical mediators that cause inflammatory side effects, in an amount sufficient for stimulating proliferation of monocytes and neutrophils.

78. The method of claim 77 wherein the β(1-3) glucan is derived from yeast.

79. The method of claim 78, wherein the yeast is a strain of *Saccharomyces cerevisiae*.

80. A method for treating refractory infections comprising administering to an animal or human an antimicrobial agent and an underivatized, aqueous soluble β(1-3)-glucan in a triple helix conformation, said glucan capable of enhancing immune response without stimulating production of biochemical mediators that cause inflammatory side effects.

81. A composition comprising an anti-microbial agent and an underivatized, aqueous soluble β(1-3)-glucan in a triple helix conformation having immunostimulating properties, which does not stimulate or prime the production of interleukin-1 or tumor necrosis factor, or both, in vitro.

82. The composition of claim 81 further comprising a physiologically acceptable vehicle.

83. The composition of claim 82 wherein the physiologically acceptable vehicle is selected from the group consisting of water, sterile saline, phosphate buffered saline, isotonic saline and dextrose.

84. The composition of claim 82 wherein the composition is in the form of a liquid, tablet, gel, ointment, lotion, capsule, powder, solution, emulsion or cream.

85. The composition of claim 81 wherein the β(1-3) glucan is derived from yeast.

86. The composition of claim 85 wherein the yeast is a strain of *Saccharomyces cerevisiae*.

87. The composition of claim 86 wherein *Saccharomyces cerevisiae* is strain R4 (NRRL Y-15903) or strain R4 Ad (ATCC 74181).

* * * * *